United States Patent
Wang et al.

(10) Patent No.: US 11,629,333 B2
(45) Date of Patent: Apr. 18, 2023

(54) GAMMA DELTA T CELLS AND A METHOD OF AUGMENTING THE TUMORICIDAL ACTIVITY OF THE SAME

(71) Applicant: Agency for Science, Technology and Research, Singapore (SG)

(72) Inventors: Shu Wang, Singapore (SG); Wei Xia Ang, Singapore (SG); Jieming Zeng, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 274 days.

(21) Appl. No.: 16/484,427

(22) PCT Filed: Feb. 8, 2018

(86) PCT No.: PCT/SG2018/050055
§ 371 (c)(1),
(2) Date: Aug. 7, 2019

(87) PCT Pub. No.: WO2018/147805
PCT Pub. Date: Aug. 16, 2018

(65) Prior Publication Data
US 2020/0032207 A1 Jan. 30, 2020

(30) Foreign Application Priority Data
Feb. 8, 2017 (SG) .......................... 10201701009Q

(51) Int. Cl.
| | | |
|---|---|---|
| *C12N 5/0783* | (2010.01) | |
| *A61P 35/00* | (2006.01) | |
| *A61K 35/17* | (2015.01) | |
| *C07K 14/435* | (2006.01) | |
| *C07K 14/725* | (2006.01) | |
| *C07K 14/705* | (2006.01) | |
| *C07K 16/28* | (2006.01) | |
| *C12N 15/85* | (2006.01) | |

(52) U.S. Cl.
CPC ............ *C12N 5/0636* (2013.01); *A61K 35/17* (2013.01); *A61P 35/00* (2018.01); *C07K 14/435* (2013.01); *C07K 14/7051* (2013.01); *C07K 14/70596* (2013.01); *C07K 16/2809* (2013.01); *C12N 15/85* (2013.01); *C07K 2319/02* (2013.01); *C07K 2319/03* (2013.01); *C12N 2501/998* (2013.01); *C12N 2501/999* (2013.01); *C12N 2502/30* (2013.01)

(58) Field of Classification Search
None
See application file for complete search history.

(56) References Cited

U.S. PATENT DOCUMENTS

| | | | | |
|---|---|---|---|---|
| 2016/0175358 A1* | 6/2016 | Jakobovits | .............. | A61P 35/00 |
| | | | | 424/93.2 |
| 2019/0119634 A1* | 4/2019 | Jakobovits | .............. | A61P 35/00 |

FOREIGN PATENT DOCUMENTS

| | | |
|---|---|---|
| CN | 105112370 A * | 12/2015 |
| CN | 105624107 A | 6/2016 |
| WO | WO-2015/061694 A2 | 4/2015 |
| WO | WO-2016/166544 A1 | 10/2016 |
| WO | WO-2017/197347 A1 | 11/2017 |

OTHER PUBLICATIONS

Google Patents English language translation of CN105112370A, published Dec. 2, 2015, pp. 1-13, downloaded Oct. 21, 2021. (Year: 2021).*
Todd et al. (Drugs. Jun. 1989;37(6):871-99). (Year: 1989).*
Lehner et al. (PLoS ONE 7(2): e31210, 2012). (Year: 2012).*
Rischer et al. (British Journal of Haematology, 126, 583-592, 2004). (Year: 2004).*
Niu et al., BMC Immunology (2015) 16:61. (Year: 2015).*
Du, S-H. et al., Co-Expansion of Cytokine-Induced Killer Cells and Vγ9Vδ2 T Cells for CAR T-Cell Therapy, PLos One, 11(9): e0161820 1-22 (2016).
International Search Report for PCT/SG2018/050055, 6 pages (dated Apr. 30, 2018).
Mirzaei, H.R. et al., Prospects for chimeric antigen receptor (CAR) [gamma][delta] T cells: A potential game changer for adoptive T cell cancer immunotherapy, Cancer Letters, 380: 413-423 (2016).
Rincon-Orozxo, B. et al., Activation of Vγ9Vδ2 T Cells by NKG2D, J. Immunol., 175(4): 2144-2151 (2005).
Sentman, NKG2D CARs as cell therapy for cancer, Cancer J, 20(2): 156-159 (2014).
Song, D-G. et al., Chimeric NKG2D CAR-Expressing T Cell-Mediated Attack of Human Ovarian Cancer is enhanced by Histone Deacetylase Inhibition, Human Gene Therapy, 24: 295-305 (2013).
Written Opinion for PCT/SG2018/050055, 9 pages (dated Apr. 30, 2018).
Xiao, L. et al., Large-scale expansion of Vγ9Vδ2 T cells with engineered K562 feeder cells in G-Rex vessels and their use as chimeric antigen receptor-modified effector cells, Cytotherapy, 20(3): 420-435 (2018).
Chinese Office Action with Search Report dated Nov. 25, 2022 for Chinese Application No. 201880023646.8.

* cited by examiner

*Primary Examiner* — Zachary S Skelding
(74) *Attorney, Agent, or Firm* — JCIP; Joseph G. Chu; Jeremy I. Maynard

(57) ABSTRACT

The present invention relates to a method of generating γδ T cells having at least one down-regulated co-inhibitory receptor, the method comprising the steps of: (a) culturing a population of cells comprising γδ T cells with a phosphoantigen to expand the γδ T cells; and (b) culturing the expanded γδ T cells with artificial antigen-presenting cells expressing a Fc receptor, and an anti-CD3 antibody. The present invention also relates to γδ T cells generated according to a method of the present invention, as well as methods of treatment and medical uses thereof.

14 Claims, 11 Drawing Sheets

Specification includes a Sequence Listing.

SEQUENCE LISTING

<160> NUMBER OF SEQ ID NOS: 12

<210> SEQ ID NO 1
<211> LENGTH: 374
<212> TYPE: PRT
<213> ORGANISM: Homo sapiens

<400> SEQUENCE: 1

```
Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
```

```
                115                 120                 125
Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
                180                 185                 190

Val Leu Asn Ala Ser Val Thr Ser Pro Leu Leu Glu Gly Asn Leu Val
                195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
                260                 265                 270

Ser Pro Glu Leu Glu Leu Gln Val Leu Gly Leu Gln Leu Pro Thr Pro
    275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
                340                 345                 350

Cys Gln Glu Gln Lys Glu Glu Gln Leu Gln Glu Gly Val His Arg Lys
    355                 360                 365

Glu Pro Gln Gly Ala Thr
    370

<210> SEQ ID NO 2
<211> LENGTH: 171
<212> TYPE: PRT
<213> ORGANISM: Homo sapiens

<400> SEQUENCE: 2

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
                20                  25                  30

Val Phe Val Asn Cys Asn Thr Ser Ile Thr Trp Val Glu Gly Thr Val
                35                  40                  45

Gly Thr Leu Leu Ser Asp Ile Thr Arg Leu Asp Leu Gly Lys Arg Ile
            50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
                100                 105                 110
```

```
Ile Ala Thr Leu Leu Ala Leu Gly Val Phe Cys Phe Ala Gly His
            115                 120                 125

Glu Thr Gly Arg Leu Ser Gly Ala Ala Asp Thr Gln Ala Leu Leu Arg
130                 135                 140

Asn Asp Gln Val Tyr Gln Pro Leu Arg Asp Arg Asp Ala Gln Tyr
145                 150                 155                 160

Ser His Leu Gly Gly Asn Trp Ala Arg Asn Lys
                165                 170

<210> SEQ ID NO 3
<211> LENGTH: 213
<212> TYPE: PRT
<213> ORGANISM: Mus musculus

<400> SEQUENCE: 3

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 4
<211> LENGTH: 450
<212> TYPE: PRT
<213> ORGANISM: Mus musculus

<400> SEQUENCE: 4

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45
```

```
Gly Tyr Ile Asn Pro Ser Arg Gly Tyr Thr Asn Tyr Asn Gln Lys Phe
     50                  55                  60
Lys Asp Lys Ala Thr Leu Thr Thr Asp Lys Ser Ser Thr Ala Tyr
 65              70                  75                  80
Met Gln Leu Ser Ser Leu Thr Ser Glu Asp Ser Ala Val Tyr Tyr Cys
                 85                  90                  95
Ala Arg Tyr Tyr Asp Asp His Tyr Cys Leu Asp Tyr Trp Gly Gln Gly
             100                 105                 110
Thr Thr Leu Thr Val Ser Ser Ala Lys Thr Thr Ala Pro Ser Val Tyr
             115                 120                 125
Pro Leu Ala Pro Val Cys Gly Gly Thr Thr Gly Ser Ser Val Thr Leu
 130                 135                 140
Gly Cys Leu Val Lys Gly Tyr Phe Pro Glu Pro Val Thr Leu Thr Trp
 145                 150                 155                 160
Asn Ser Gly Ser Leu Ser Ser Gly Val His Thr Phe Pro Ala Val Leu
                 165                 170                 175
Gln Ser Asp Leu Tyr Thr Leu Ser Ser Val Thr Val Thr Ser Ser
                 180                 185                 190
Thr Trp Pro Ser Gln Ser Ile Thr Cys Asn Val Ala His Pro Ala Ser
             195                 200                 205
Ser Thr Lys Val Asp Lys Lys Ile Glu Pro Arg Pro Lys Ser Cys Asp
 210                 215                 220
Lys Thr His Thr Cys Pro Pro Cys Pro Ala Pro Glu Leu Leu Gly Gly
 225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
             275                 280                 285
Asn Ala Lys Thr Lys Pro Arg Glu Glu Gln Tyr Asn Ser Thr Tyr Arg
 290                 295                 300
Val Val Ser Val Leu Thr Val Leu His Gln Asp Trp Leu Asn Gly Lys
 305                 310                 315                 320
Glu Tyr Lys Cys Lys Val Ser Asn Lys Ala Leu Pro Ala Pro Ile Glu
                 325                 330                 335
Lys Thr Ile Ser Lys Ala Lys Gly Gln Pro Arg Glu Pro Gln Val Tyr
             340                 345                 350
Thr Leu Pro Pro Ser Arg Asp Glu Leu Thr Lys Asn Gln Val Ser Leu
             355                 360                 365
Thr Cys Leu Val Lys Gly Phe Tyr Pro Ser Asp Ile Ala Val Glu Trp
 370                 375                 380
Glu Ser Asn Gly Gln Pro Glu Asn Asn Tyr Lys Thr Thr Pro Pro Val
 385                 390                 395                 400
Leu Asp Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
             420                 425                 430
Glu Ala Leu His Asn His Tyr Thr Gln Lys Ser Leu Ser Leu Ser Pro
             435                 440                 445
Gly Lys
 450
```

<210> SEQ ID NO 5
<211> LENGTH: 144
<212> TYPE: PRT
<213> ORGANISM: Homo sapiens

<400> SEQUENCE: 5

Ile Trp Ser Ala Val Phe Leu Asn Ser Leu Phe Asn Gln Glu Val Gln
1               5                   10                  15

Ile Pro Leu Thr Glu Ser Tyr Cys Gly Pro Cys Pro Lys Asn Trp Ile
            20                  25                  30

Cys Tyr Lys Asn Asn Cys Tyr Gln Phe Phe Asp Glu Ser Lys Asn Trp
        35                  40                  45

Tyr Glu Ser Gln Ala Ser Cys Met Ser Gln Asn Ala Ser Leu Leu Lys
    50                  55                  60

Val Tyr Ser Lys Glu Asp Gln Asp Leu Leu Lys Leu Val Lys Ser Tyr
65                  70                  75                  80

His Trp Met Gly Leu Val His Ile Pro Thr Asn Gly Ser Trp Gln Trp
                85                  90                  95

Glu Asp Gly Ser Ile Leu Ser Pro Asn Leu Leu Thr Ile Ile Glu Met
            100                 105                 110

Gln Lys Gly Asp Cys Ala Leu Tyr Ala Ser Ser Phe Lys Gly Tyr Ile
        115                 120                 125

Glu Asn Cys Ser Thr Pro Asn Thr Tyr Ile Cys Met Gln Arg Thr Val
    130                 135                 140

<210> SEQ ID NO 6
<211> LENGTH: 164
<212> TYPE: PRT
<213> ORGANISM: Homo sapiens

<400> SEQUENCE: 6

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 7
<211> LENGTH: 113
<212> TYPE: PRT
<213> ORGANISM: Homo sapiens

<400> SEQUENCE: 7

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys

<210> SEQ ID NO 8
<211> LENGTH: 21
<212> TYPE: PRT
<213> ORGANISM: Homo sapiens

<400> SEQUENCE: 8

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 9
<211> LENGTH: 34
<212> TYPE: DNA
<213> ORGANISM: Artificial Sequence
<220> FEATURE:
<223> OTHER INFORMATION: Forward primer with SphI site

<400> SEQUENCE: 9
gcgcgcatgc cttcaaccaa gaagttcaaa ttcc                                34

<210> SEQ ID NO 10
<211> LENGTH: 46
<212> TYPE: DNA
<213> ORGANISM: Artificial Sequence
<220> FEATURE:
<223> OTHER INFORMATION: Reverse primer with NheI site

<400> SEQUENCE: 10
acgaagctag ccacagtcct ttgcatacag atgtacgtat ttggag                  46

<210> SEQ ID NO 11
<211> LENGTH: 41
<212> TYPE: DNA
<213> ORGANISM: Artificial Sequence
<220> FEATURE:
<223> OTHER INFORMATION: Forward primer CMV-F

<400> SEQUENCE: 11
atccgctcga gtagttatta atagtaatca attacggggt c                       41

<210> SEQ ID NO 12
<211> LENGTH: 150

```
<212> TYPE: DNA
<213> ORGANISM: Artificial Sequence
<220> FEATURE:
<223> OTHER INFORMATION: Reverse Primer T150-R

<400> SEQUENCE: 12
tttttttttt tttttttttt tttttttttt tttttttttt tttttttttt tttttttttt      60
tttttttttt tttttttttt tttttttttt tttttttttt tttttttttt tttttttttt     120
tttttttttt tttttttttt tttttttttt                                      150
```

GAMMA DELTA T CELLS AND A METHOD OF AUGMENTING THE TUMORICIDAL ACTIVITY OF THE SAME

CROSS REFERENCE TO RELATED APPLICATIONS

This application claims priority to Singapore application No. 10201701009Q, filed 8 Feb. 2017, the contents of which are incorporated herein by reference.

TECHNICAL FIELD OF THE INVENTION

The present invention relates to gamma delta T cells and their uses thereof, and a method of generating gamma delta T cells. More particularly, the present invention relates to gamma delta T cells having improved tumoricidal activity and their uses thereof, and a method of generating gamma delta T cells having improved tumoricidal activity.

BACKGROUND OF THE INVENTION

The following discussion of the background to the invention is intended to facilitate understanding of the present invention. However, it should be appreciated that the discussion is not an acknowledgment or admission that any of the material referred to was published, known or a part of the common general knowledge in any jurisdiction as at the priority date of the application.

Gamma delta (γδ) T cells are a minor population in the peripheral blood (0.5-10% of T cells in healthy adults) that express γδ heterodimer of T cell receptor (TCR) chains and play an important role in linking innate and adaptive immune responses. The majority of peripheral blood γδ T cells express the variable-gene segments Vγ9 and Vδ2 (Vγ9Vδ2 T cells). In a non-major histocompatibility complex (MHC) restricted manner, γδ T cells can be activated by recognizing and interacting with a set of tumor-associated antigens, including phosphoantigens that are produced during metabolic dysregulation in tumour cells, lipids presented by CD1 family members, and cell stress markers. The activated γδ T cells release abundant inflammatory cytokines interferon (IFN)-γ and tumour necrosis factor (TNF)-α, and use both perforin and granzyme B secretory pathway and death receptor (Fas/Fas-ligand, TRAIL/TRAIL-receptor) pathway to execute the killing of tumor cells. γδ T cells have been indicated to be able to kill many different types of tumor cell lines and tumor in vivo and in vitro, including leukemia, neuroblastoma and various carcinomas. As such, the development of γδ T cells that are suitable for cancer treatment is desirable.

In addition to TCR, γδ T cells express the natural killer group 2D (NKG2D) receptor, killer-cell immunoglobulin-like receptors (KIRs), and many co-inhibitory receptors that can play either co-stimulatory or inhibitory roles to affect their tumoricidal activity. The balance between activating signals and inhibitory signals induced by their respective receptors has profound effects on the activation of γδ T cells.

The NKG2D receptor is an activating receptor expressed by human natural killer (NK) cells, γδ T cells, CD8+ T cells, and NKT cells. This receptor can interact with eight stress-induced ligands belonging to two families: two MHC class I chain-related proteins MICA and MICB and six HCMV UL16-binding proteins (ULBP1-6). The NKG2D ligands are not usually expressed on healthy tissues but can be up-regulated upon DNA damage, infection and transformation of cells, thus being commonly detected on hematopoietic tumors and carcinomas. Because of the tumour-associated over-expression, the NKG2D ligands have been a favourable therapeutic target for anticancer strategies.

Thus, there exists a need to develop γδ T cells and a method of augmenting the tumoricidal activity of γδ T cells to facilitate the use of γδ T cells for treatment of cancer.

SUMMARY OF THE INVENTION

The present invention seeks to address and/or ameliorate the problems in the prior art by providing a method of generating gamma delta T cells and augmenting and/or enhancing their functions.

In an aspect of the present invention, there is provided a method of generating γδ T cells having at least one down-regulated co-inhibitory receptor, the method comprising the steps of: (a) culturing a population of cells comprising γδ T cells with a phosphoantigen to expand the γδ T cells; and (b) culturing the expanded γδ T cells with artificial antigen-presenting cells expressing a Fc receptor, and an anti-CD3 antibody.

Preferably, the Fc receptor is CD64.

Preferably, the phosphoantigen is zoledronic acid or a salt thereof. More preferably, the phosphoantigen is added in an amount of 5 μM.

Preferably, the population of cells are peripheral blood mononuclear cells.

Preferably, the method does not require an initial depletion step to enrich the peripheral blood mononuclear cells.

Preferably, the γδ T cells are of the Vγ9Vδ2 subtype.

Preferably, step (a) is carried out for 7 days. More preferably, step (b) is carried out for 10 days. Even more preferably, the method comprises passaging the cells every 2 to 3 days.

Preferably, the artificial antigen-presenting cells are K562 cells. Preferably, the method further comprises irradiating the artificial antigen-presenting cells prior to step (b) using gamma irradiation.

Preferably, the anti-CD3 antibody is Muromonab-CD3.

Preferably, the co-inhibitory receptors are at least one co-inhibitory receptor selected from the group consisting of cytotoxic T lymphocyte (CTL)-associated antigen 4 (CTLA-4/CD152); programmed cell death protein 1 (PD-1/CD279); lymphocyte activation gene-3 (LAG-3); T cell immunoglobulin and immunoreceptor tyrosine-based inhibition motif (ITIM) domain (TIGIT); T-cell immunoglobulin and mucin-containing protein 3 (TIM3); and B and T lymphocyte attenuator (BTLA).

Preferably, another portion of the phosphoantigen is added simultaneously with step (b).

Preferably, the method further comprises modifying the γδ T cells having at least one down-regulated co-inhibitory receptor to express a chimeric antigen receptor (CAR). Preferably, the modified γδ T cells have at least one up-regulated activating receptor. More preferably, modifying the γδ T cells comprises transfecting the γδ T cells with an mRNA vector encoding the CAR. Preferably, transfecting the γδ T cells comprises RNA electroporation.

Preferably, the CAR comprises an extracellular antigen binding domain of natural killer group 2D (NKG2D). More preferably, the γδ T cells overexpresses NKG2D.

Preferably, the CAR comprises a signalling domain of CD3 zeta or DAP 12. More preferably, the CAR comprises an extracellular antigen binding domain of NKG2D and a signalling domain of DAP12.

In another aspect of the present invention, there is provided a γδ T cell having at least one down-regulated co-inhibitory receptor generated by a method according to an aspect of the present invention.

In another aspect of the present invention, there is provided a γδ T cell having at least one down-regulated co-inhibitory receptor and modified to express a chimeric antigen receptor (CAR), wherein the CAR comprises an extracellular antigen binding domain of NKG2D and a signalling domain of CD3 zeta or DAP 12. Preferably, the signalling domain is DAP12.

In another aspect of the present invention, there is provided a method of treating cancer comprising the step of administering a therapeutically effective amount of γδ T cells according to an aspect of the present invention. Preferably, the cancer is colorectal or ovarian cancer or any other cancer expressing NKG2D ligands.

In another aspect of the present invention, there is provided a γδ T cell according to an aspect of the present invention for use in treating cancer.

In another aspect of the present invention, there is provided a γδ T cell according to an aspect of the present invention for use in the treatment of colorectal or ovarian cancer or any other cancer expressing NKG2D ligands.

In another aspect of the present invention, there is provided a use of a γδ T cell according to an aspect of the present invention in the manufacture of a medicament for the treatment of cancer. Preferably, the cancer is colorectal cancer or ovarian cancer or any other cancer expressing NKG2D ligands.

In another aspect of the present invention, there is provided a method of treating a patient with cancer comprising the steps of: administering to the patient, a therapeutically effective amount of γδ T cells having at least one down-regulated co-inhibitory receptor generated by a method comprising the steps of: (a) culturing a population of cells comprising γδ T cells with a phosphoantigen; (b) culturing the expanded γδ T cells with artificial antigen-presenting cells expressing a Fc receptor, and an anti-CD3 antibody. Preferably, said method comprises administering the γδ T cells having at least one down-regulated co-inhibitory receptor to the patient by intraperitoneal injection.

In another aspect of the present invention, there is provided a method of treating cancer in a patient, the method comprising the steps of: (a) obtaining peripheral blood mononuclear cells (PBMCs) comprising γδ T cells from the patient; (b) culturing the PBMCs with a phosphoantigen to expand the γδ T cells; (c) culturing the PBMCs with the expanded γδ T cells, with an artificial antigen-presenting cells expressing a Fc receptor, and an anti-CD3 antibody against CD3 to generate γδ T cells with at least one down-regulated co-inhibitory receptor; and (d) administering the γδ T cells with at least one down-regulated co-inhibitory receptor to the patient.

Preferably, the Fc receptor is CD64.

Preferably, the phosphoantigen is zoledronic acid or a salt thereof.

Preferably, the phosphoantigen is added in an amount of 5 μM.

Preferably, the method does not require an initial depletion step to enrich the peripheral blood mononuclear cells.

Preferably, the γδ T cells are of the Vγ9Vδ2 subtype.

Preferably, step (b) is carried out for 7 days.

Preferably, step (c) is carried out for 10 days.

Preferably, the method comprises passaging the cells every 2 to 3 days.

Preferably, the artificial antigen-presenting cells are K562 cells.

Preferably, the method further comprises irradiating the artificial antigen-presenting cells prior to step (c) using gamma irradiation.

Preferably, the anti-CD3 antibody is Muromonab-CD3.

Preferably, the at least one co-inhibitory receptor is selected from the group consisting of cytotoxic T lymphocyte (CTL)-associated antigen 4 (CTLA-4/CD152); programmed cell death protein 1 (PD-1/CD279); lymphocyte activation gene-3 (LAG-3); T cell immunoglobulin and immunoreceptor tyrosine-based inhibition motif (ITIM) domain (TIGIT); T-cell immunoglobulin and mucin-containing protein 3 (TIM3); and B and T lymphocyte attenuator (BTLA).

Preferably, the method further comprises modifying the γδ T cells having at least one down-regulated co-inhibitory receptor to express a chimeric antigen receptor (CAR).

Preferably, the modified γδ T cells have at least one up-regulated activating receptor.

Preferably, modifying the γδ T cells comprises transfecting the γδ T cells with an mRNA vector encoding the CAR.

Preferably, transfecting the γδ T cells comprises RNA electroporation.

Preferably, the CAR comprises an extracellular antigen binding domain of natural killer group 2D (NKG2D).

Preferably, the γδ T cells overexpresses NKG2D.

Preferably, the CAR comprises a signalling domain of CD3 zeta or DAP 12.

Preferably, the CAR comprises an extracellular antigen binding domain of NKG2D and a signalling domain of DAP12.

BRIEF DESCRIPTION OF THE DRAWINGS

The invention will now be described, by way of example only, with reference to the accompanying drawings, in which:

FIG. 6A illustrates tumor burden images by bioluminescent imaging (BLI) on days 7, 28 and 42. FIG. 6B illustrates the treatment results in reduction in SKOV3 xenografts. Tumor burden over time by BLI is shown. Each mouse is represented by one line. FIG. 6C illustrates survival curves. The treatment with Vγ9Vδ2 T cells electroporated with NKG2Dz mRNA plus Zometa resulted in significant survival advantages when compared with the PBS group or the treatment with the cells electroporated with mGFP mRNA plus Zometa.

DETAILED DESCRIPTION

Particular embodiments of the present invention will now be described with reference to the accompany drawings. The terminology used herein is for the purpose of describing particular embodiments only and is not intended to limit the scope of the present invention. Additionally, unless defined otherwise, all technical and scientific terms used herein have the same meanings as commonly understood by one or ordinary skill in the art to which the present invention belongs.

Definitions

Throughout the specification, unless otherwise indicated to the contrary, the terms "comprising", "consisting of", and the like, are to be construed as non-exhaustive, or in other words, as meaning "including, but not limited to".

Throughout the specification, unless the context requires otherwise, the word "comprise" or variations such as "comprises" or "comprising", will be understood to imply the inclusion of a stated integer or group of integers but not the exclusion of any other integer or group of integers.

Throughout the specification, unless the context requires otherwise, the word "include" or variations such as "includes" or "including", will be understood to imply the inclusion of a stated integer or group of integers but not the exclusion of any other integer or group of integers.

As used herein, the term "about" typically means +/−5% of the stated value, more typically +/−4% of the stated value, more typically +/−3% of the stated value, more typically +/−2% of the stated value, even more typically +/−1% of the stated value, and even more typically +/−0.5% of the stated value.

As used herein, the connotation "1E5", "1E7", "1E8" and "1E10" refer to $1\times10^5$, $1\times10^7$, $1\times10^8$ and $1\times10^{10}$ respectively. As used herein, the term "activating receptor" has ordinary meaning in the art, and would be understood to refer to a receptor which is capable of stimulating an activation signal upon binding of its corresponding ligand. For instance, the NKG2D receptor is an activating receptor.

As used herein, the term "augmenting" when used in the context of tumoricidal activity refers to improved tumor cell killing effects. For instance, improved tumor killing effects may be measured by an increase in the median survival time of a patient. As used herein, the terms "co-inhibitory receptor" and "inhibitory receptor" have ordinary meaning in the art and would be understood to refer to receptors that are capable of stimulating an inhibitory or blocking signal upon binding of their corresponding ligands. The terms "co-inhibitory receptor" and "inhibitory receptor" are used interchangeably in the specification herein.

As used herein, the term "co-stimulatory" refers to a molecule that binds to a receptor on a T cell that is involved in the activation of the T cell.

Figure 1A:
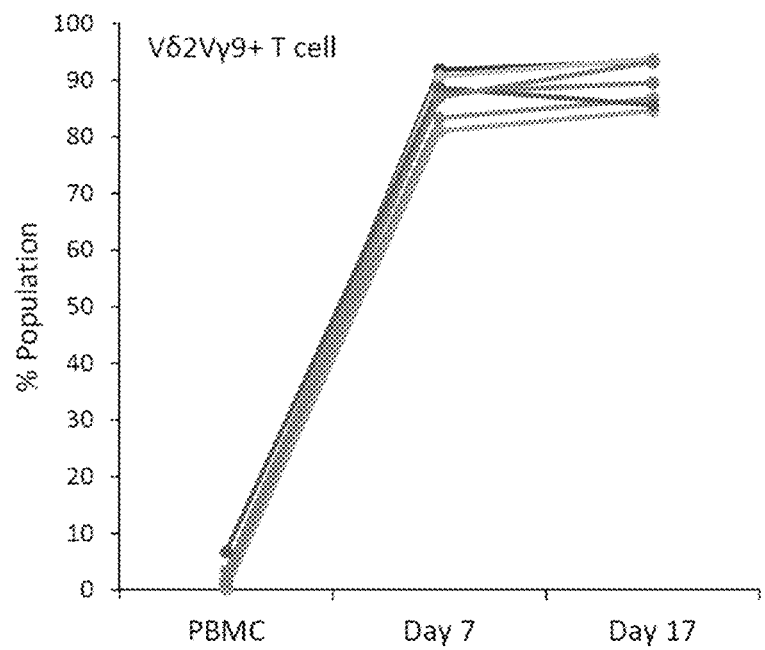
FIGS. 1A to 1D (collectively referred to as "FIG. 1") show the characterization of the cells expanded with Zometa, OKT3 and gamma-irradiated K562 aAPCs. Human PBMCs were first expanded with Zometa for 7 days, followed by treatment with Zometa, OKT3 and gamma-irradiated K562 aAPCs for another 10 days. Frequencies of Vγ9Vδ2 T cells (FIG. 1A), NKG2D-positive cells (FIG. 1B), CD3-positive alpha beta T cells (FIG. 1C) and CD3-negative, CD56-positive NK cells (FIG. 1D) in PBMCs, on day 7 and day 17 analyzed by flow cytometry are shown. PBMC samples from 7 donors were tested and each sample is represented by one line.
Figure 1B:
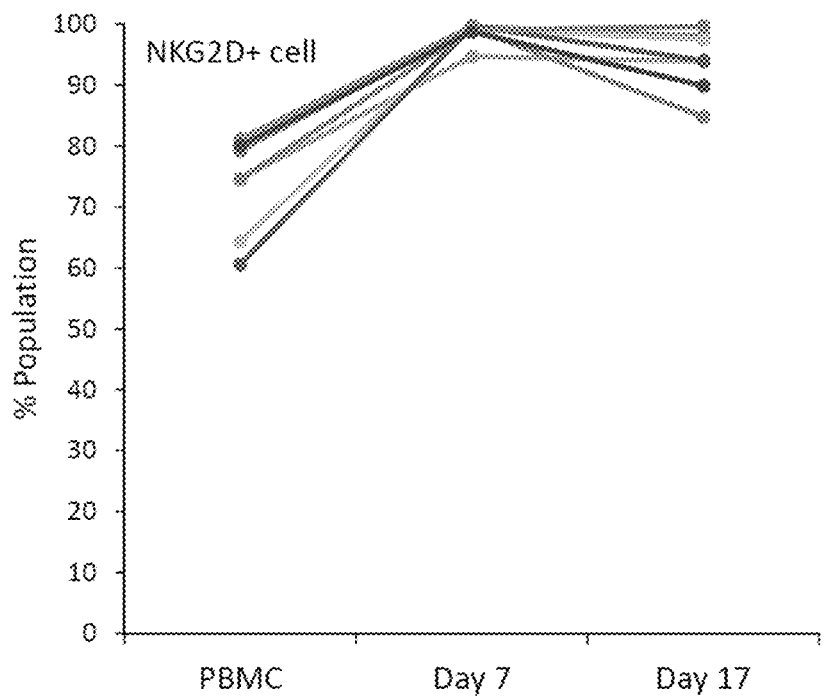
Figure 1C:
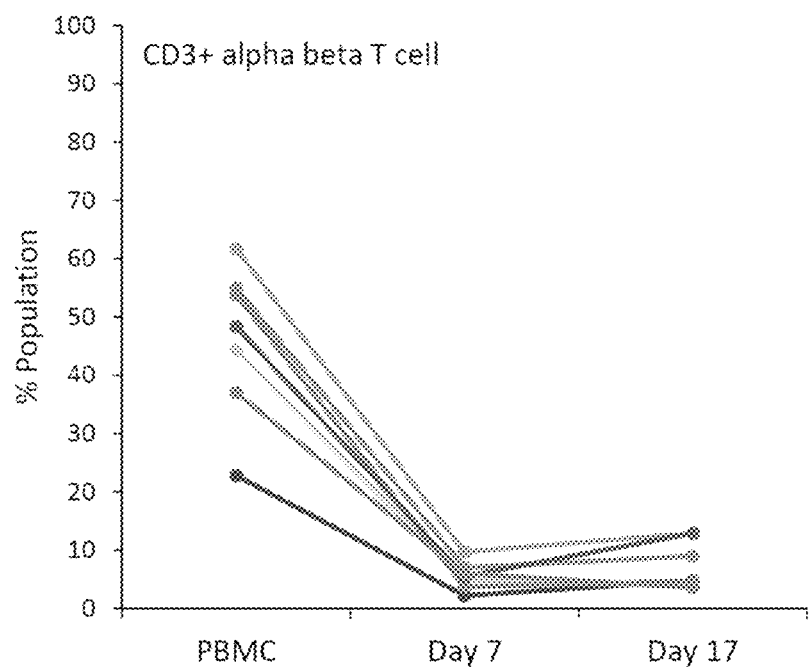
Figure 1D:
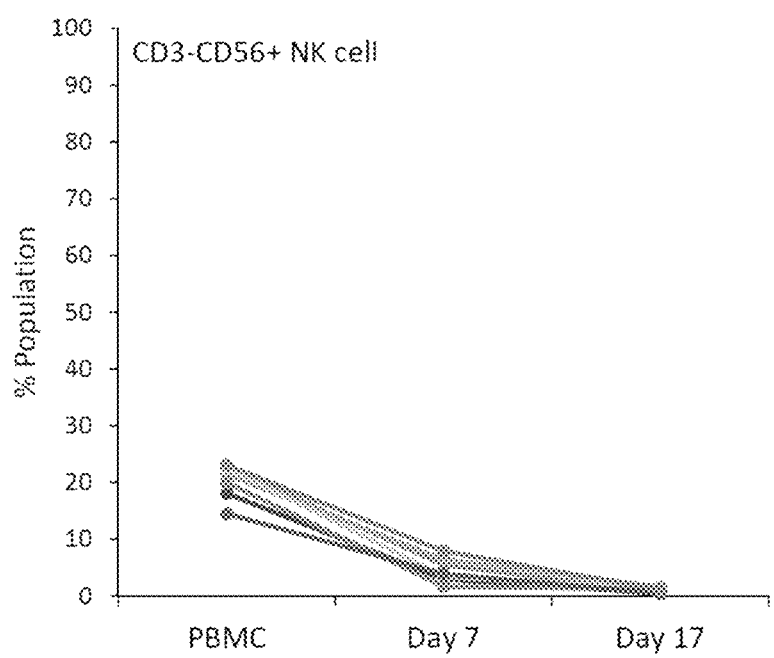
Figure 2A:
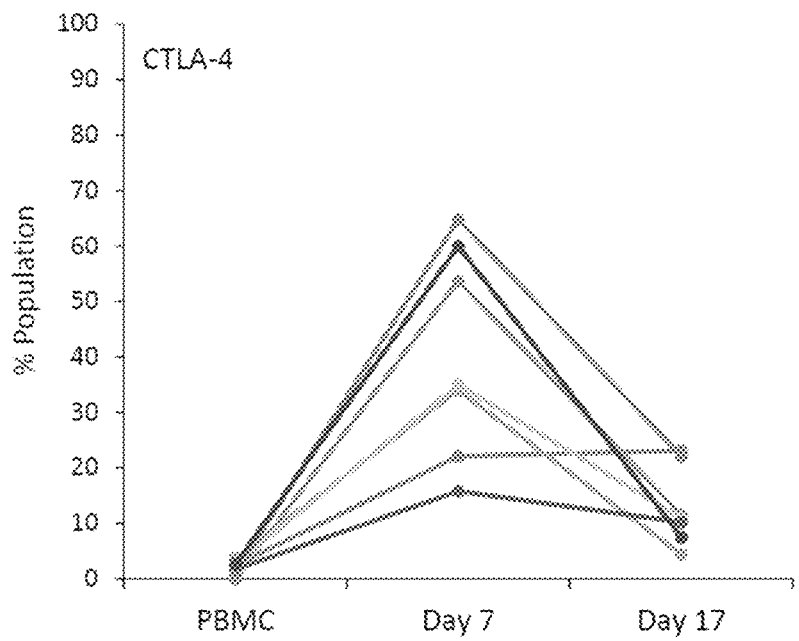
FIGS. 2A to 2F (collectively referred to as "FIG. 2") show the expression of co-inhibitory receptors CTLA-4 (FIG. 2A), PD-1 (FIG. 2B), LAG-3 (FIG. 2C), TIGIT (FIG. 2D), TIM-3 (FIG. 2E) and BTLA (FIG. 2F) on PBMCs and the expanded cells. Human PBMCs were first expanded with Zometa for 7 days, followed by treatment with Zometa, OKT3 and gamma-irradiated K562 aAPCs for another 10 days. The expression frequencies of 6 co-inhibitory receptors on PBMCs and on the expanded cells collected on day 7 and day 17 analyzed by flow cytometry are shown. PBMC samples from 7 donors were tested and each sample is represented by one line.
Figure 2B:
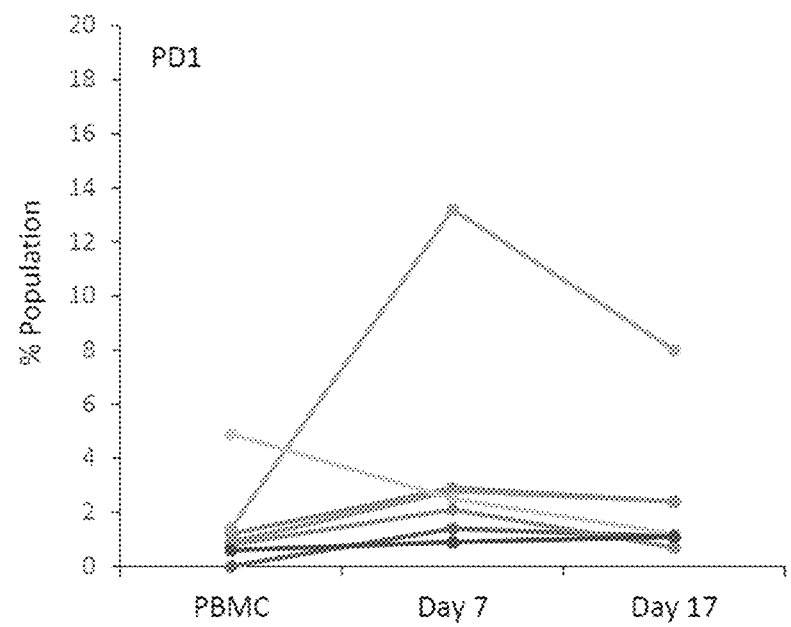
Figure 2C:
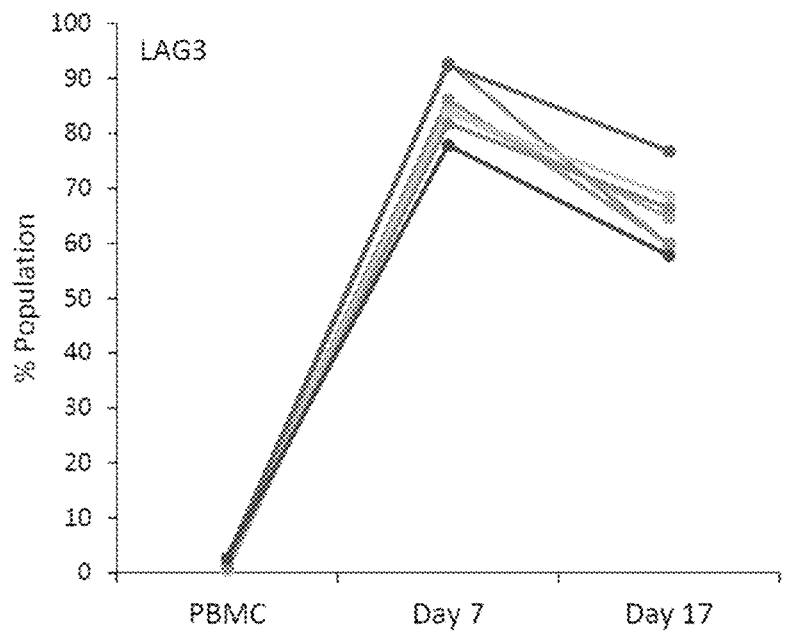
Figure 2D:
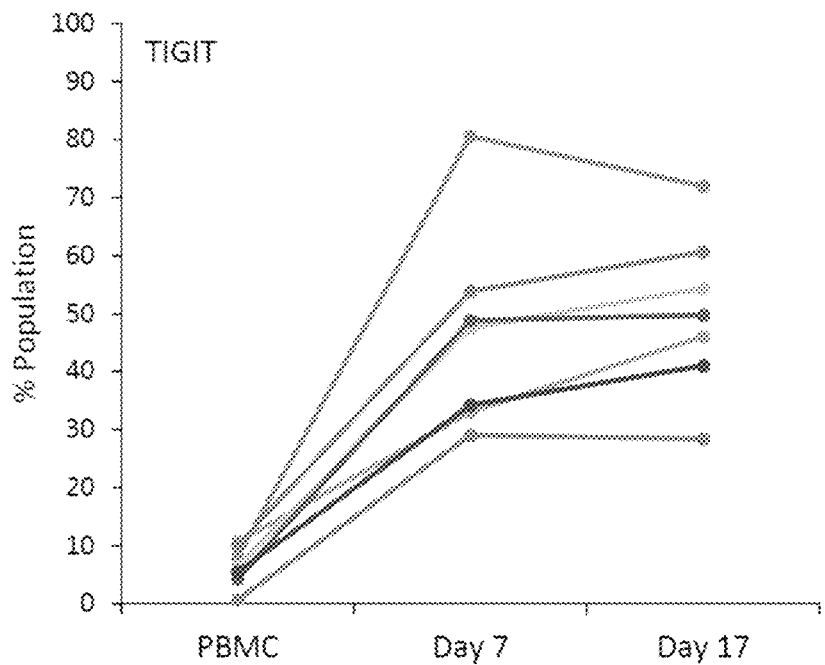
Figure 2E:
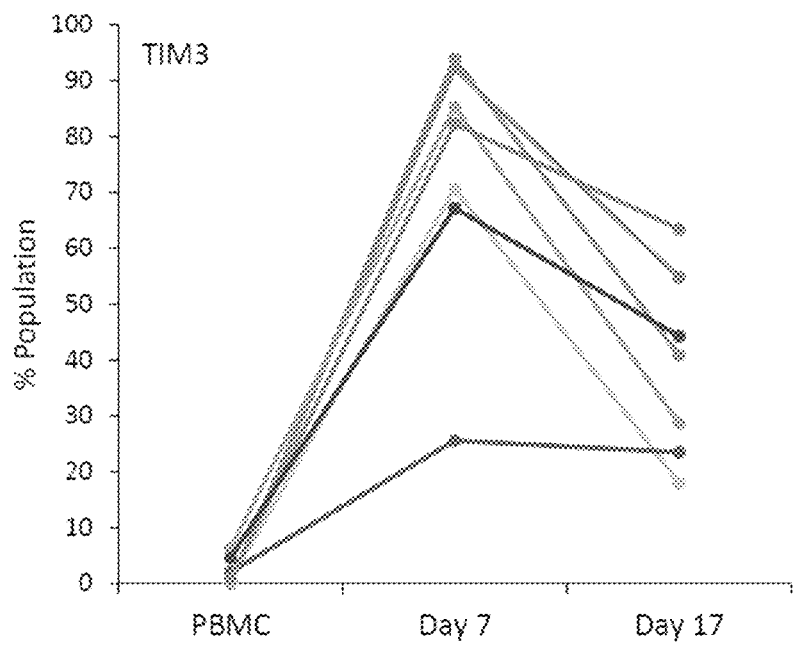
Figure 2F:
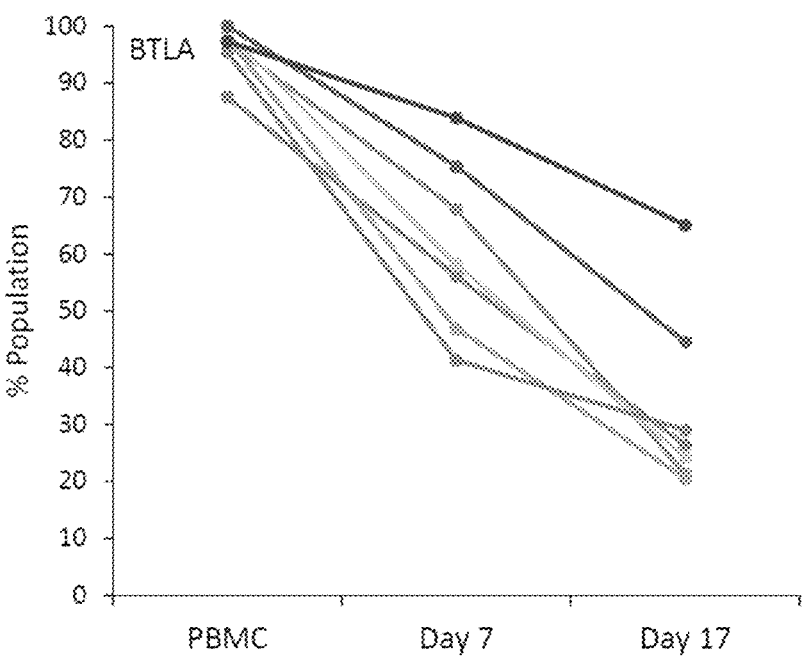

As used herein, the term "down-regulation" or "down-regulated" when used in the context of receptors refers to a decrease in the expression of the receptors. A non-limiting example is illustrated in FIG. 2C, where the expression level of co-inhibitory receptor LAG-3 on Vγ9Vδ2 T cells after culturing said T cells with an anti-CD3 (OKT3 clone) antibody and gamma-irradiated CD64-expressing K562 aAPCs, is generally lower than the expression level of LAG-3 before the T cells are cultured with the anti-CD3 antibody and K562 aAPCs, but after expanding the Vγ9Vδ2 T cells in a sample of PBMCs using Zometa.

As used herein, the term "Fc receptor" or "FcR" is a receptor that binds to the Fc region of an immunoglobulin (Ig). Fc receptors are found on many cells which participate in immune responses. Among the human FcRs that have been identified so far are those which recognize IgG (designated FcγR), IgE (FcεRI), IgA (FcαR), and polymerized IgM/A (FcεμR). FcRs are found in the following cell types: FcεRI (mast cells), FcεRII (many leukocytes), FcαR (neutrophils), and FcμR (glandular epithelium, hepatocytes). (Hogg *Immunol. Today* 9: 185-86 (1988)). The widely studied FcγRs are central in cellular immune defenses, and are responsible for stimulating the release of mediators of inflammation and hydrolytic enzymes involved in the pathogenesis of autoimmune disease. (Unkeless, *Annu. Rev. Immunol.* 6: 251-87 (1988)). The FcγRs provide a crucial link between effector cells and the lymphocytes that secrete Ig, since the macrophage/monocyte, polymorphonuclear leukocyte, and natural killer (NK) cell FcγRs confer an element of specific recognition mediated by IgG. Human leukocytes have at least three different receptors for IgG: hFcμRI (found on monocytes/macrophages), hFcγRII (on monocytes, neutrophils, eosinophils, platelets, possibly B cells, and the K562 cell line), and FcγIII (on NK cells, neutrophils, eosinophils, and macrophages).

As used herein, the term "median survival time" refers to a parameter that is commonly used for evaluating therapeutic effects and is the time after which 50% of a patient group with a particular condition are still living and 50% have died. For instance, the median survival time of a patient group with a particular condition, such as tumor-bearing mice, is 73 days after treatment with CAR-modified γδ T cells.

As used herein, the term "major histocompatibility complex" or "MHC" is a specific cluster of genes, many of which encode evolutionarily related cell surface proteins involved in antigen presentation, which are among the most important determinants of histocompatibility. Class I MHC, or MHC-I, function mainly in antigen presentation to CD8 T lymphocytes. Class II MHC, or MHC-II, function mainly in antigen presentation to CD4 T lymphocytes. The MHC gene, located on chromosome 6, includes HLA genes divided into distinct regions including Class I genes that encode for a heavy chain polypeptide located in the HLA-A, B and C regions; and Class II genes including the D region which is subdivided in three main regions, DP, DQ and DR, each containing genes for a number of α and β chains. A complete listing of current HLA specificities, any of which may be used in the present immunovaccines, and corresponding sequences, both nucleotide and amino acid, can be located at the IMGT/HLA Database at "http://www.ebi-.ac.uk/imgt/hla" which provides a database for sequences of the human major histocompatibility complex (HLA) and includes the official sequences for the WHO Nomenclature Committee For Factors of the HLA System. The IMGT/HLA Database is part of the international ImMunoGeneTics project.

As used herein, the term "up-regulation" or "up-regulated" when used in the context of receptors refers to an increase in the expression of the receptors. A non-limiting example is illustrated in FIG. 2C, where the expression level of co-inhibitory receptor LAG-3 on Vγ9Vδ2 T cells after expanding the Vγ9Vδ2 T cells in a sample of PBMCs using Zometa, is higher than the expression level of LAG-3 before treatment with Zometa.

As used herein, the term "treatment", "treat" and "therapy", and synonyms thereof refer to both therapeutic treatment and prophylactic or preventative measures, wherein the object is to prevent or slow down (lessen) a disease, for example cancer. Those in need of such treatment include those already with a disease as well as those prone to getting the disease or those in whom a disease is to be prevented.

As used herein, the term "therapeutically effective amount" of a compound will be an amount of active agent that is capable of preventing or at least slowing down (lessening) a disease, e.g. cancer. Dosages and administration of compounds, compositions and formulations of the present invention may be determined by one of ordinary skill in the art of clinical pharmacology or pharmacokinetics. See, for example, Mordenti and Rescigno, (1992) Pharmaceutical Research. 9:17-25; Morenti et al., (1991) Pharmaceutical Research. 8:1351-1359; and Mordenti and Chappell, "The use of interspecies scaling in toxicokinetics" in Toxicokinetics and New Drug Development, Yacobi et al. (eds) (Pergamon Press: NY, 1989), pp. 42-96. An effective amount of the active agent of the present invention to be employed therapeutically will depend, for example, upon the therapeutic objectives, the route of administration, and the condition of the patient. As used in the specification herein, the term "patient" includes humans and animals. Accordingly, it will be necessary for the therapist to titer the dosage and modify the route of administration as required to obtain the optimal therapeutic effect. A typical dosage per infusion may range from about 1E5 cells to up to 1E10 cells of the patient's body weight or more per day, preferably about 1E3 cells/kg/infusion to 1E8 cells/kg/infusion.

As used herein, a polynucleotide is said to "encode" a polypeptide if, in its native state or when manipulated by methods well known to those skilled in the art, it can be transcribed and/or translated to produce the mRNA for and/or the polypeptide or a fragment thereof. Polynucleotides include but are not limited to DNA (e.g. cDNA) and RNA (e.g. mRNA). The anti-sense strand is the complement of such a nucleic acid, and the encoding sequence can be deduced therefrom.

As used herein, a nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, natural amino acids, etc.), polypeptides with substituted linkages as well as other modifications known in the art, both naturally and non-naturally occurring.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

In the context of the present invention, a homologous sequence is taken to include an amino acid sequence which is at least 60, 70, 80 or 90% identical, preferably at least 95 or 98% identical at the amino acid level over at least 20, 50, 100, 200, 300 or 400 amino acids with the amino acid sequences set out in sequence listings. In particular, homology should typically be considered with respect to those regions of the sequence known to be essential for the function of the protein rather than non-essential.

Although homology can also be considered in terms of similarity (i.e. amino acid residues having similar chemical properties/functions), in the context of the present invention it is also possible to express homology in terms of sequence identity. The terms "substantial homology" or "substantial identity", when referring to polypeptides, indicate that the polypeptide or protein in question exhibits at least about 70% identity with an entire naturally-occurring protein or a portion thereof, usually at least about 80% identity, and preferably at least about 90 or 95% identity.

Homology comparisons can be conducted by eye, or more usually, with the aid of readily available sequence comparison programs. These commercially available computer programs can calculate % homology between two or more sequences.

Percentage (%) homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

The present invention provides for polyclonal and/or monoclonal antibodies and fragments thereof, and immunologic binding equivalents thereof, which are capable of specifically binding to a polypeptide target and fragments thereof. Such antibodies thus include for example, but are not limited to, polyclonal, monoclonal, chimeric, single chain, Fab fragments, and a Fab expression library.

A "monoclonal antibody" refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bi-specific (chimeric) monoclonal antibody.

Throughout this disclosure, certain embodiments may be disclosed in a range format. It should be understood that the description in range format is merely for convenience and brevity and should not be construed as a limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. Ranges are not limited to integers, and can include decimal measurements. This applies regardless of the breadth of the range.

EMBODIMENTS OF THE INVENTION

In an aspect of the present invention, there is provided a method of generating γδ T cells having at least one down-regulated co-inhibitory receptor, the method comprising the steps of: (a) culturing a population of cells comprising γδ T cells with a phosphoantigen to expand the γδ T cells; and (b) culturing the expanded γδ T cells with artificial antigen-presenting cells expressing a Fc receptor, and an anti-CD3 antibody. Consequently, the expression of at least one co-stimulatory and/or inhibitory receptors of γδ T cells are manipulated, particularly by the manipulation of the expression of functional receptors expressed on the surface of γδ T cells, thereby facilitating the use of γδ T cells for treatment of cancer. Advantageously, there may be up-regulated expression of activating receptors and down-regulated expression of co-inhibitory receptors in the γδ T cells. Preferably, there is an up-regulation of the expression of at least one co-inhibitory receptor during the step of culturing the population of cells comprising γδ T cells with a phosphoantigen to expand the γδ T cells; and there is a down-regulation of the expression of at least one co-inhibitory receptor during the step of culturing the expanded γδ T cells with artificial antigen-presenting cells expressing a Fc receptor, and an anti-CD3 antibody.

Advantageously, the method of the present invention makes use of γδ TCRs that recognize cancer-associated antigens in an HLA (human leukocyte antigen)-independent manner. In contrast, αβ TCRs do not recognize cancer-associated antigens in an HLA-independent manner. As such, γδ T cells generated in the present invention may be used in the development of "off-the-shelf" therapeutics. Importantly, for cancer treatment, γδ T cells are capable of infiltrating a range of human malignancies, a capacity required critically for them to interact with and kill cancer cells. These malignancies include renal, bladder, ovarian, colorectal, breast and nasopharyngeal carcinomas.

More advantageously, the method of the present invention is less time consuming, less complicated and at least as effective as prior art methods. For instance, methods of modifying γδ T cells such as CRISPR/Cas9, which makes use of a gene editing nuclease, are time consuming and complicated.

In various embodiments, the γδ T cells are Vγ9Vδ2 T cells, preferably pure Vγ9Vδ2 T cells. Certain earlier studies relate to expansion of polyclonal γδ T cells, not a single subtype of γδ T cells, meaning that the polyclonal γδ T cell population generated may contain a mixture of many subtypes of γδ T cells. Various problems may arise from the use of other methods in view of the following considerations:

1) the benefits of using γδ T cells expressing polyclonal repertoire of γ and δ TCR chains have yet to be thoroughly investigated since very little is known about human γδ T cells expressing TCR γδ alleles other than Vδ1 and Vδ2;
2) emerging pathogenic roles of γδ T cells in cancer progression have been reported, which are mainly attributed to IL17+γδ T cell subsets; and
3) since adult human peripheral blood Vγ9Vδ2 T cells distinctly express Th1 signature and 50-80% produce IFNγ but only <5% produce IL17, the present invention preferably relates to the expansion of Vγ9Vδ2 T cells, particularly pure Vγ9Vδ2 T cells. The Vγ9Vδ2 T subpopulation of γδ T cells have been reported to be highly cytotoxic to a wide range of tumour cells.

In a preferred embodiment, the method of the present invention relates to the manipulation of the expression of functional receptors expressed on the surface of Vγ9Vδ2 T cells. Advantageously, there may be up-regulated expression of activating receptors and down-regulated expression of co-inhibitory receptors in the Vγ9Vδ2 T cells. Preferably, there is an up-regulation of the expression of at least one co-inhibitory receptor during the step of culturing the population of cells comprising Vγ9Vδ2 T cells with a phosphoantigen to expand the Vγ9Vδ2 T cells; and there is a down-regulation of the expression of at least one co-inhibitory receptor during the step of culturing the expanded Vγ9Vδ2 T cells with artificial antigen-presenting cells expressing a Fc receptor, and an anti-CD3 antibody.

Inhibitory receptors (or co-inhibitory receptors), also named as immune checkpoint receptors, can down-regulate immune responses to avoid excessive immune activation, providing a critical role in the maintenance of immune homeostasis. The co-inhibitory receptors expressed on γδ T cells include cytotoxic T lymphocyte (CTL)-associated antigen 4 (CTLA-4, CD152), programmed cell death protein 1 (PD-1, CD279), lymphocyte activation gene-3 (LAG-3), T-cell immunoglobulin and mucin-containing protein (TIM-3), T cell immunoglobulin and immunoreceptor tyrosine-based inhibition motif (ITIM) domain (TIGIT), and B and T lymphocyte attenuator (BTLA). Advantageously, the method of the present invention led to down-regulation or reduced expression of co-inhibitory receptors, thereby leading to improved tumor killing effects. In particular, the method of the present invention led to the reduced expression of at least one inhibitory receptor selected from the group consisting of CTLA-4, CD152, PD1, LAG-3, TIGIT, TIM3 and BTLA. In a preferred embodiment, the method of the present invention led to the reduced expression of two, three, four, five or six co-inhibitory receptors. In a more preferred embodiment, the method of the present invention led to the reduced expression of six co-inhibitory receptors.

In addition to TCR, γδ T cells express the natural killer group 2D (NKG2D) receptor, killer-cell immunoglobulin-like receptors (KIRs), and many co-inhibitory receptors that can play either co-stimulatory or inhibitory roles to affect their tumoricidal activity. The balance between activating signals and inhibitory signals induced by their respective receptors has profound effects on the activation of γδ T cells. The NKG2D receptor is an activating receptor expressed by human natural killer (NK) cells, γδ T cells, CD8+ T cells, and NKT cells. This receptor can interact with eight stress-induced ligands belonging to two families: two MHC class I chain-related proteins MICA and MICB and six HCMV UL16-binding proteins (ULBP1-6). The NKG2D ligands are not usually expressed on healthy tissues but can be up-regulated upon DNA damage, infection and transformation of cells, thus being commonly detected on hematopoietic tumors and carcinomas. Because of the tumour-associated over-expression, the NKG2D ligands have been a favourable therapeutic target for anticancer strategies. Advantageously, the method of the present invention led to the reduced expression of co-inhibitory receptors without obvious effects on NKG2D expression.

In various embodiments, the γδ T cells, in particular, Vγ9Vδ2 T cells, may be expanded from peripheral blood mononuclear cells (PBMCs), cord blood mononuclear cells (CBMCs) or tissue derived cells in a chemically defined culture medium which can include, but is not limited to, RPMI, TexMACS, IMDM, CTS OpTmizer or AIM-V media. In a preferred embodiment, the Vγ9Vδ2 T cells are expanded from PBMCs seeded in AIM-V media. Isolated PBMCs may be freshly isolated or cryopreserved prior to expansion in the culture medium. In a more preferred embodiment, the PBMCs are seeded in AIM-V media at a density of 2E6. As such, in various embodiments, the method further comprises seeding the PBMCs in a serum-free lymphocyte-activation medium, such as AIM-V media.

In various embodiments, the cell culture medium may be supplemented with fetal calf serum (FCS), human AB serum, autologous plasma, human platelet lysate or a chemically defined serum replacement substitutes. In various embodiments, the serum/plasma/substitute may be added in an amount of about 0.1 to about 20% (v/v), about 1 to about 10% (v/v), or about 1 to about 5% (v/v) to the culture solution. In a preferred embodiment, human AB serum is added in about 5% v/v.

In various embodiments, the method comprises passaging the cells every day, every 2 days, every 3 days or every 4 days, preferably every 2 to 3 days.

Because of their infrequent nature, Vγ9Vδ2 T cells need to be expanded from PBMCs for adoptive T cell therapy. In various embodiments, step (a) further comprises adding the phosphoantigen into the sample of PBMCs. In various embodiments, the population of cells comprising γδ T cells is cultured with the phosphoantigen to expand the γδ T cells for about 5 days to about 10 days, preferably about 7 days. In various embodiments, the phosphoantigen is added in an amount of about 0.1 to about 10 μM, about 1 to about 10 μM or about 1 to about 5 μM. In a preferred embodiment, the phosphoantigen is zoledronic acid or zoledronate (Zometa) or salts thereof. The formula for zoledronate is as follows.

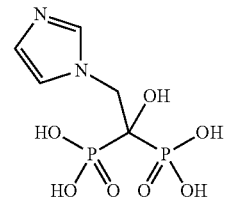 [SMILES: O=P(O)(O)C(O)(Cn1ccnc1)P(=O)(O)O]

The phosphoantigen may be a synthetic antigen such as isopentenyl pyrophosphate (IPP), phosphostim/bromohydrin pyrophosphate (BrHPP), (E)-4-Hydroxy-3-methyl-but-2-enyl pyrophosphate (HMBPP) or DMAPP.

In a more preferred embodiment, Zometa is added in an amount of 5 μM. Advantageously, a small amount (1 μM or 5 μM) of Zometa leads to vigorous proliferation of Vγ9Vδ2 T cells in vitro in response to the phosphoantigen, Zometa, which is an FDA-approved, commercially available bisphosphonate drug that has been used to treat patients with postmenopausal osteoporosis. Zometa can inhibit farnesyl pyrophosphate synthase, an enzyme acting downstream of isopentenyl pyrophosphate (IPP) in the mevalonate pathway, thus profoundly increasing intracellular levels of IPP.

In various embodiments, the cytokine IL-2 is also added with the phosphoantigen. In various embodiments, IL-2 is added in a concentration of about 50 IU/ml to about 1000 IU/ml, about 100 IU/ml to about 500 IU/m or about 200 IU/ml to about 400 IU/ml. In a preferred embodiment, IL-2 is added in a concentration of about 300 IU/ml.

In various embodiments, the method does not require an initial depletion step to enrich the sample of PBMCs. As such, the method of the present invention leads to a savings in time and money because the PBMCs can be expanded without undergoing an initial depletion step.

In various embodiments, the Vγ9Vδ2 T cells are activated by using an artificial antigen-presenting cell (aAPC) and an antibody against CD3, homologous peptides, or a portion or a polypeptide fragment thereof. In various embodiments, the expanded γδ T cells is cultured with artificial antigen-presenting cells expressing a Fc receptor, and an anti-CD3 antibody between about 10 days to about 21 days or longer, preferably between about 10 days to about 14 days. The anti-CD3 antibody may be a monoclonal and/or polyclonal antibody or fragments thereof, or immunologic binding equivalents thereof capable of binding CD3, homologous peptides, or a portion or a polypeptide fragment thereof. Surprisingly, the inventors found that co-inhibitory receptors were up-regulated on Vγ9Vδ2 T cells when expanding Vγ9Vδ2 T cells in the sample of peripheral blood mononuclear cells using the phosphoantigen. Advantageously, activating the Vγ9Vδ2 T cells using the artificial antigen-presenting cell together with an antibody against CD3 led to down-regulation of the co-inhibitory receptor expression on Vγ9Vδ2 T cells. In addition, there was improved tumor cell killing effects as compared with Vγ9Vδ2 T cells collected after treatment with the phophoantigen. Without being bound by theory, it is believed that conformational change of the CD3 co-receptor on T cells and aAPCs, in particular K562-based aAPCs, advantageously affect the tumor killing activity of Vγ9Vδ2 T cells. As such, the combination of expanding Vγ9Vδ2 T cells in the sample of PBMCs using a phosphoantigen and activating the Vγ9Vδ2 T cells using an artificial antigen-presenting cell together with an antibody against CD3 led to an unexpected technical advantage. In particular, the Vγ9Vδ2 T cells were effectively expanded and augmented to exhibit enhanced tumor cell killing activity.

As used herein, artificial antigen presenting cells (aAPCs) are mimetic cells that are modelled after antigen presenting cells, and provide T cell stimulation signals. In various embodiments, the aAPC is derived from a human erythro-leukemia cell line, such as the K562 cell line. Advantageously, K562 cells expresses neither endogenous HLA class I and II molecules, nor co-stimulatory molecules such as CD86, CD83, 4-1BBL, OX40L, ICOSL (B7H2, B7RP1) or CD40L, thereby minimizing unintended allogeneic responses. Among three human IgG Fc receptors, K562 cells endogenously expresses a high level of CD32 but not CD16 or CD64. K562 cells also express adhesion molecules CD54 (ICAM-1) and CD58 (LFA-3), which enhances K562 cells interactions with T cells and improves T cell stimulation. Furthermore, K562 cells can be easily manipulated for stable expression of transgenes and have been found safe in clinical trials when used as feeder cells for T cell expansion. In a preferred embodiment, the aAPC expresses CD64 (SEQ ID NO: 1), homologous polypeptides, or a portion or a polypeptide fragment thereof.

In various embodiments, the method further comprises irradiating the aAPC prior to step (b) using gamma irradiation.

In various embodiments, the antibody against CD3 (SEQ ID NO: 2) is Muromonal-CD3 (tradename OKT3; light chain SEQ ID NO: 3; heavy chain SEQ ID NO: 4). Without being bound by theory, it is believed that the antigen-binding sites of OKT3 can interact with CD3 on the γδ T cell surface to induce the conformational change of the co-receptor. Advantageously, the Fc-portion of OKT-3 can attach to CD64 expressed on the K562 cells because of the high affinity between the Fc-portion of OKT-3 for CD64. As such, down-regulation of the co-inhibitory receptors was observed, thereby leading to improved tumor killing effects.

In various embodiments, the method further comprises modifying the γδ T cells using a chimeric antigen receptor (CAR). Advantageously, the method led to further enhanced tumor killing. In various embodiments, treatment with CAR-modified γδ T cells resulted in the increase of the median survival time of tumor-bearing mice. The median survival time of such mice increased from 41 to 51 days in the control groups, to 73 days after treatment with CAR-modified Vγ9Vδ2 T cells (FIG. 6C). Preferably, the increase in median survival time is in the range of about 40% to about 80%, such as but not limited to at least about 40%, about 45%, about 50%, about 55%, about 60%, about 65%, about 70%, about 75%, or about 80%. Treatment with CAR-modified Vγ9Vδ2 T cells resulted in a prolonged survival time of more than 70 days in tumor-bearing mice (FIG. 6C). In various embodiments, the survival time was increased to about 80 days. As such, modifying the γδ T cells using a CAR led to enhanced tumor killing because the median survival time of tumor-bearing mice increased by about 78% and about 43% compared to the PBS control group and the mGFP control respectively.

In various embodiments, the CAR comprises an extracellular antigen binding domain of NKG2D (SEQ ID NO: 5), homologous polypeptides, or a portion or a polypeptide fragment thereof. As such, γδ T cells with an up-regulated NKG2D function are obtained. The NKG2D extracellular domain acts as the target recognition domain to bind the NKG2D ligands on tumor cells. Consequently, the interaction activates γδ cells through the intracellular signaling motif, thereby leading to enhanced tumor killing.

In various embodiments, the CAR comprises a signalling domain of CD3 zeta or DAP 12 (NKG2Dz or NKG2Dp, respectively; CD3 zeta SEQ ID NO: 6; DAP 12 SEQ ID NO: 7), homologous polypeptides, or a portion or a polypeptide fragment of CD3 zeta or DAP 12. Advantageously, the tumor-killing efficacy of the Vγ9Vδ2 T cells can be further enhanced. In particular, the tumor-killing efficacy of the Vγ9Vδ2 T cells is enhanced through the modification of the effector cells with gene transfer of NKG2Dz.

In various embodiments, the CAR comprises a transmembrane domain of CD8-α (CD8-β) chain (SEQ ID NO: 8), homologous polypeptides, or a portion or a polypeptide fragment thereof.

In a preferred embodiment, the CAR comprises an extracellular antigen binding domain of NKG2D and an intracellular signalling domain of DAP12, homologous polypeptides, or a portion or a polypeptide fragment of NKG2D or DAP 12.

In another aspect of the present invention, there is provided a γδ T cell having at least one down-regulated co-inhibitory receptor generated by a method according to an aspect of the present invention.

In another aspect of the present invention, there is provided a γδ T cell having at least one down-regulated co-inhibitory receptor and modified to express a chimeric antigen receptor (CAR), wherein the CAR comprises an extracellular antigen binding domain of NKG2D and an intracellular signalling domain of CD3 zeta or DAP 12. Preferably the signalling domain is DAP12.

In another aspect of the present invention, there is provided a method of treating cancer comprising administering a therapeutically effective amount of γδ T cells according to an aspect of the present invention. Preferably, the cancer is colorectal or ovarian cancer or any other cancer expressing NKG2D ligands.

In another aspect of the present invention, there is provided a γδ T cell according to an aspect of the present invention for use in treating cancer. Preferably, the cancer is colorectal cancer or ovarian cancer or any other cancer expressing NKG2D ligands.

In another aspect of the present invention, there is provided use of a γδ T cell according to an aspect of the present invention in the manufacture of a medicament for the treatment of cancer. Preferably, the cancer is colorectal cancer or ovarian cancer or any other cancer expressing NKG2D ligands.

In another aspect of the present invention, there is provided a method of treating a patient with cancer comprising: administering to the patient, a therapeutically effective amount of γδ T cells having at least one down-regulated co-inhibitory receptor generated by a method comprising the steps of: (a) culturing a population of cells comprising γδ T cells with a phosphoantigen; (b) culturing the expanded γδ T cells with artificial antigen-presenting cells expressing a Fc receptor, and an anti-CD3 antibody. Preferably, said method comprises administering the γδ T cells having at least one down-regulated co-inhibitory receptor to the patient by intraperitoneal injection.

In another aspect of the present invention, there is provided a method of treating cancer in a patient, the method comprising the steps of: (a) obtaining peripheral blood mononuclear cells (PBMCs) comprising γδ T cells from the patient; (b) culturing the PBMCs with a phosphoantigen to expand the γδ T cells; (c) culturing the PBMCs with the expanded γδ T cells, with an artificial antigen-presenting cells expressing a Fc receptor, and an anti-CD3 antibody against CD3 to generate γδ T cells with at least one down-regulated co-inhibitory receptor; and (d) administering the γδ T cells with at least one down-regulated co-inhibitory receptor to the patient.

Other aspects of the invention will become apparent to those of ordinary skill in the art upon review of the following description of specific embodiments of the invention in conjunction with the accompanying figures.

EXAMPLES

Materials and Methods
Cells

Human PBMC were isolated from fresh buffy coat of healthy donors by density gradient centrifugation using Ficoll-Paque (GE Healthcare, Milwaukee, Wis.). Human myelogenous leukemia cell line K562 (ATCC) and a K562-based aAPC cell line genetically engineered for stable expression of EGFP, CD86, CD64 and 4-1BBL (Du et al., 2016) were cultured in IMDM (Lonza Biotech, Basel, Switzerland) supplemented with 10% FBS. Other tumor cell lines used in the present invention were cultured in DMEM supplemented with 10% FBS.

For Vγ9Vδ2 T cell activation and expansion, PBMCs were seeded at a density of 2E6 cells/ml in AIM-V (Life Technologies) supplemented with 5% human AB serum (Valley Biomedical, Winchester, Va.). Zometa (5 µM, Sigma Aldrich, St. Louis, Mo.) and IL-2 (300 IU/ml) were added on day 0, followed by adding 50 ng/ml anti-CD3 antibody (OKT3 clone, eBioscience, San Diego, Calif.), gamma irradiated K562 aAPCs at a 100:1 ratio, 300 IU/ml IL-2, and 5 µM Zometa from day 7 onwards. 5 µM Zometa and 300 IU/ml IL-2 on day 0 and the anti-CD3/CD28-dynabead method (Life Technologies). The culture medium was refreshed every 2 to 3 days. In other words, the cells were passaged every 2 to 3 days.

Construction of NKG2D CAR Vectors and Generation of mRNA CAR T Cells

To generate NKG2D mRNA CAR vectors, a synthetic sequence containing the T7 promoter, 5'UTR, with Kozak sequence, a multiple cloning site, the GM-CSF signal peptide encoding sequence and the alpha-globin 3'UTR sequence was synthesized and inserted into pFastbacl vector (Life Technologies) to construct the basal backbone vector pFBCMV-T7. The extracellular domain of human NKG2D (NKG2D-ED, uniprot P26718-1, amino acids 83-216) was amplified by PCR from a PMBC cDNA library using the primers 5'-gcgcgcatgccttcaaccaagaagttcaaattcc-3' (forward primer with SphI site (SEQ ID NO: 9)) and 5'-acgaagctagc-cacagtcctttgcatacagatgtacgtatttggag-3' (reverse primer with NheI site (SEQ ID NO: 10)). NKG2D chimeric proteins were constructed by fusing NKG2D-ED to the CD8a hinge and transmembrane region (CD8 H-TM, uniprot P01732 (SEQ ID NO: 8), amino acids 128-210) and CD3 (SEQ ID NO: 6) or DAP12 (SEQ ID NO: 7) signalling moiety, and then subcloned into pFBCMV-T7 with EcoRI and SalI. The mGFP control vector was generated by replacing the NKG2D ED part of the NKG2Dz vector with GFP encoding sequence (the start codon removed) by SphI and NheI.

To generate mRNA molecules encoding the NKG2D chimeric proteins, PCR was performed using the above pFBCMV-T7 vectors as DNA templates, a forward primer CMV-F (5'-atccgctcgagtagttattaatagtaatcaattacggggtc-3') (SEQ ID NO: 11) and reverse primer T150-R (SEQ ID NO: 12). Capped mRNA was generated through in vitro transcription of the PCR DNA templates using the mMESSAGE mMACHINE T7 ULTRA transcription kit (Invitrogen, Carlsbad, Calif.) or the mScript™ RNA system (Epicentre, Madison, Wis.). For mRNA transfection, Vγ9Vδ2 T cells were mixed with the generated mRNA molecules and electroporated in a 2-mm cuvette (Bio-Rad, Hercules, Calif.) using a NEPA21 electroporator (Nepagene, Chiba, Japan) with the following parameters: voltage 240 V, pulse length 4 ms, pulse once. The electroporated T cells were rested for 3 hours and stored at −80° C. until use.

Cytotoxicity Assay

The cytolytic activity of CAR-modified Vγ9Vδ2 T cells was examined with a non-radioactive method (DELFIA EuTDA Cytotoxicity Reagents kit, PerkinElmer, MA). Time-resolved fluorescence was measured in Victor3 multilabel plate counter (PerkinElmer). The effector to target (E:T) ratios used ranged from 20:1 to 2.5:1. Control groups were set up to measure spontaneous release (only target cells added), maximum release (target cells added with 10 µl lysis buffer), and medium background (no cell added). Killing efficacy was calculated by using the following formula:

$$\% \text{ Specific release} = \frac{\text{Experimental release (counts)} - \text{Spontaneous release (counts)}}{\text{Maximum release (counts)} - \text{Spontaneous release (counts)}} \times 100$$

Animal Experiment

Non-obese diabetic/severe combined immunodeficiency/IL-2Rγcnull (NSG) mice (6-8 weeks old, female) were used in the present invention. Mice were inoculated via intraperitoneal (i.p.) injection of 1E7 SKOV3-Luc cells. On day 7 post-tumor inoculation, tumor engraftment was confirmed by live bioluminescent imaging (BLI) monitored using an IVIS Spectrum Imaging platform with Living Image software (PerkinElmer). Mice with similar BLI signal intensity were randomly divided into different groups. For treatment, 1E7 modified Vγ9Vδ2 T cells or PBS cells were i.p. injected into the tumor-bearing mice, twice a week for 3 weeks. Tumor progression was monitored by BLI. All luminescent signals and images were acquired and analysed with the Xenogen living image software v2.5. Behaviour and survival of the mice were monitored closely. Humane endpoints were used and mice were euthanized by cervical dislocation under sodium pentobarbital anaesthesia upon signs of severe distress such as swollen belly due to tumor ascites formation, seizures, tremors, laboured or difficulty in breathing, significant weight loss (>15% body weight), signs of emaciation (i.e. prominent skeletal structures), impaired ambulation, inability to remain upright or evidence of moribund condition. The survival curves were established based on the dates when mice were found dead or euthanized.

Statistical Analysis

Data are presented as mean±standard deviation (SD). All statistics were performed using GraphPad Prim 5.0 (San Diego, Calif.). P values <0.05 were considered significant.

Example 1: Down-Regulation of Co-Inhibitor Receptor Expression on Vγ9Vδ2 T Cells by OKT3 and K562 aAPCs Vγ9Vδ2 T cells were efficiently expanded by treating PBMCs using 5 µM of Zometa. The Vγ9Vδ2 T-cell population was amplified from ~4% in PBMCs on day 0 to close to 90% by day 7, together with a concurrent increase of the NKG2D-positive cell population (FIG. 1).

On the other hand, the decrease in the proportion of αβ T cells to less than 10% and NK cells to less than 3% was observed on day 7. In view of the important roles of co-inhibitory receptors in cancer therapy, the expression of six of them, namely, CTLA-4, PD1, LAG3, TIGIT, TIM3, and BTLA, on the Zometa-expanded Vγ9Vδ2 T cells was examined using flow cytometry (FIG. 2). The PMBCs did not express detectable levels of the receptors, except BTLA. Surprisingly, 7 days after Zometa treatment, a significant increase of co-inhibitory receptor-expressing cells on all 7 samples was observed for 4 out of the 6 co-inhibitory receptors examined, including CTLA-4, LAG3, TIGIT and TIM3. A significant increase of PD1-positive cells was observed in one sample and a decrease was observed in another sample, whereas the remaining samples showed either minor increase or no change in the frequency of PD1-positive cells. BTLA expression was reduced after Zometa treatment for 7 days.

Given the findings that the tumor killing activity of γδ T cells can be regulated by the conformational change of the CD3 co-receptor on T cells and that K562-based aAPCs can be used to activate and propagate the proliferation of polyclonal γδ T cells, the inventors tested whether the combined use of the two treatments can affect the expression of co-inhibitory receptors on γδ T cells.

Figure 7:
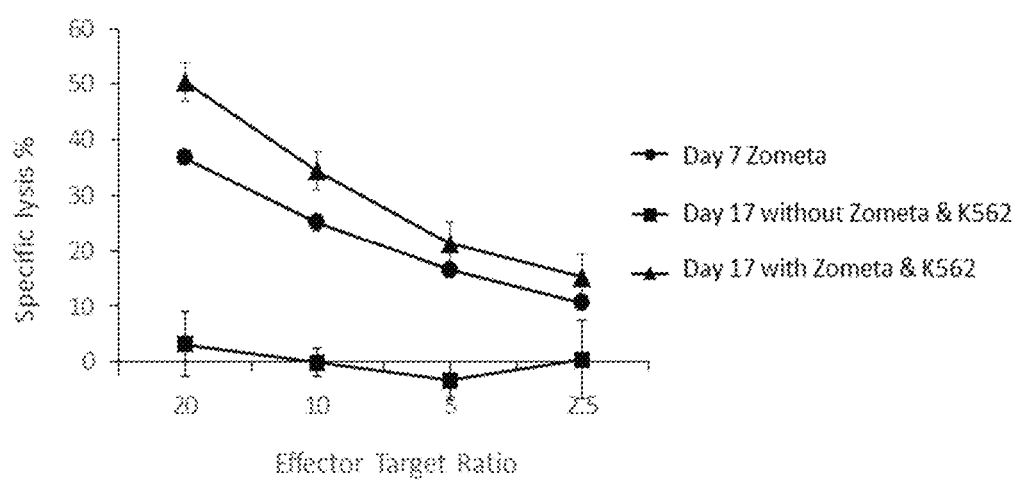
FIG. 7 shows the cytotoxicity of Day 7 and Day 17 Vγ9Vδ2 T cells against SKOV3 ovarian cancer cells. Vγ9Vδ2 T cells obtained after the co-culture with K562 cells (Day 17 with Zometa & K562) displayed improved tumor cell killing effects compared with Vγ9Vδ2 T cells collected after Zometa treatment for 7 days only (Day 7 Zometa). Cells collected after Day 17 without Zometa and K562 cells were used as the control (Day 17 without Zometa & K562).

After the initial treatment of PBMCs with Zometa for 7 days, an anti-CD3 (OKT3 clone) antibody and gamma-irradiated CD64-expressing K562 aAPCs, as well as another portion of Zometa, were added to the culture and the cells were further cultured for another 10 days. Without being bound by theory, it is believed that the Fc-portion of OKT-3 can attach to CD64 (the high affinity human IgG receptor FcγRI) expressed on K562 cells, whereas the antigen-binding sites of OKT3 can interact with CD3 on the γδ T cell surface to induce the conformational change of the co-receptor. This cell-cell interaction between CD3+ γδ T cells and CD64+ K562 aAPCs provides co-stimulatory signal-2, leading to γδ T cell activation and proliferation, likely without triggering their anergy or apoptosis. Advantageously, numerical expansion of T cells were observed after this combined treatment for 10 days and Vγ9Vδ2 T cells were expanded more than 1000-fold during the co-culture period. Importantly, down-regulation of all 6 examined co-inhibitory receptors on γδ T cells was observed, without obvious effects on NKG2D expression (FIGS. 1 and 2). In addition, Vγ9Vδ2 T cells obtained after the co-culture displayed improved tumor cell killing effects compared with Vγ9Vδ2 T cells collected after Zometa treatment for 7 days only (FIG. 7).

Example 2: Gene Transfer of NKG2Dz to Enhance Tumor Killing Effects of Vγ9Vδ2 T Cells To further improve the tumor cell killing activity of Vγ9Vδ2 T cells obtained with the co-cultured method of the present invention, the inventors proceeded to test equipping Vγ9Vδ2 T cells by over-expressing an activating receptor on their surface. In particular, electroporation of mRNA encoding an activating receptor into the expanded Vγ9Vδ2 T cells was carried out.

Figure 3:
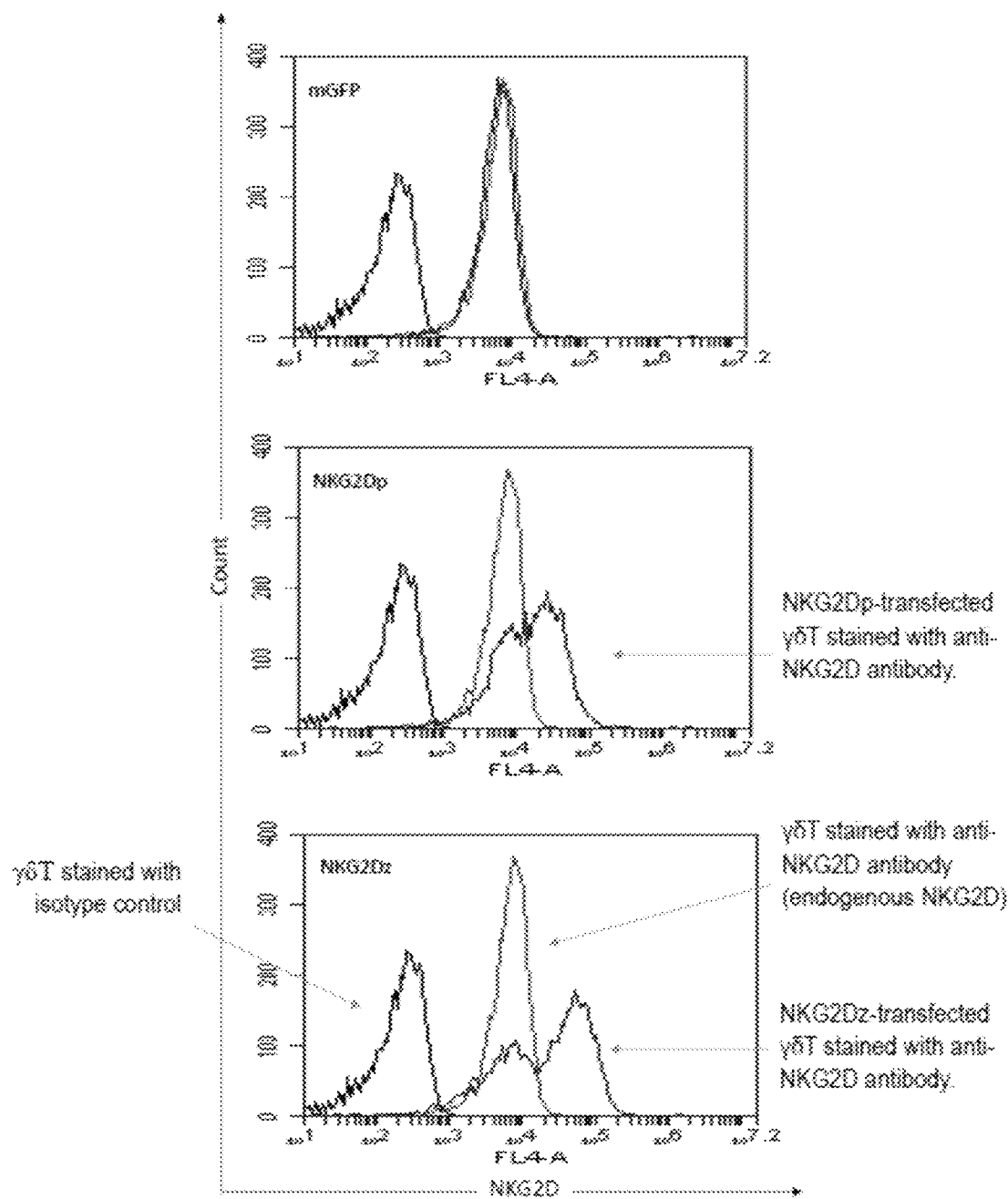
FIG. 3 shows the expression of NKG2D chimeric proteins on Vγ9Vδ2 T cells. Flow cytometric analysis was performed with an anti-NKGD antibody or an isotype control antibody to detect the surface expression of NKG2D on Vγ9Vδ2 T cells or cells electroporated with mGFP, NKG2Dp or NKG2Dz mRNA 24 hours ago.
Figure 4:
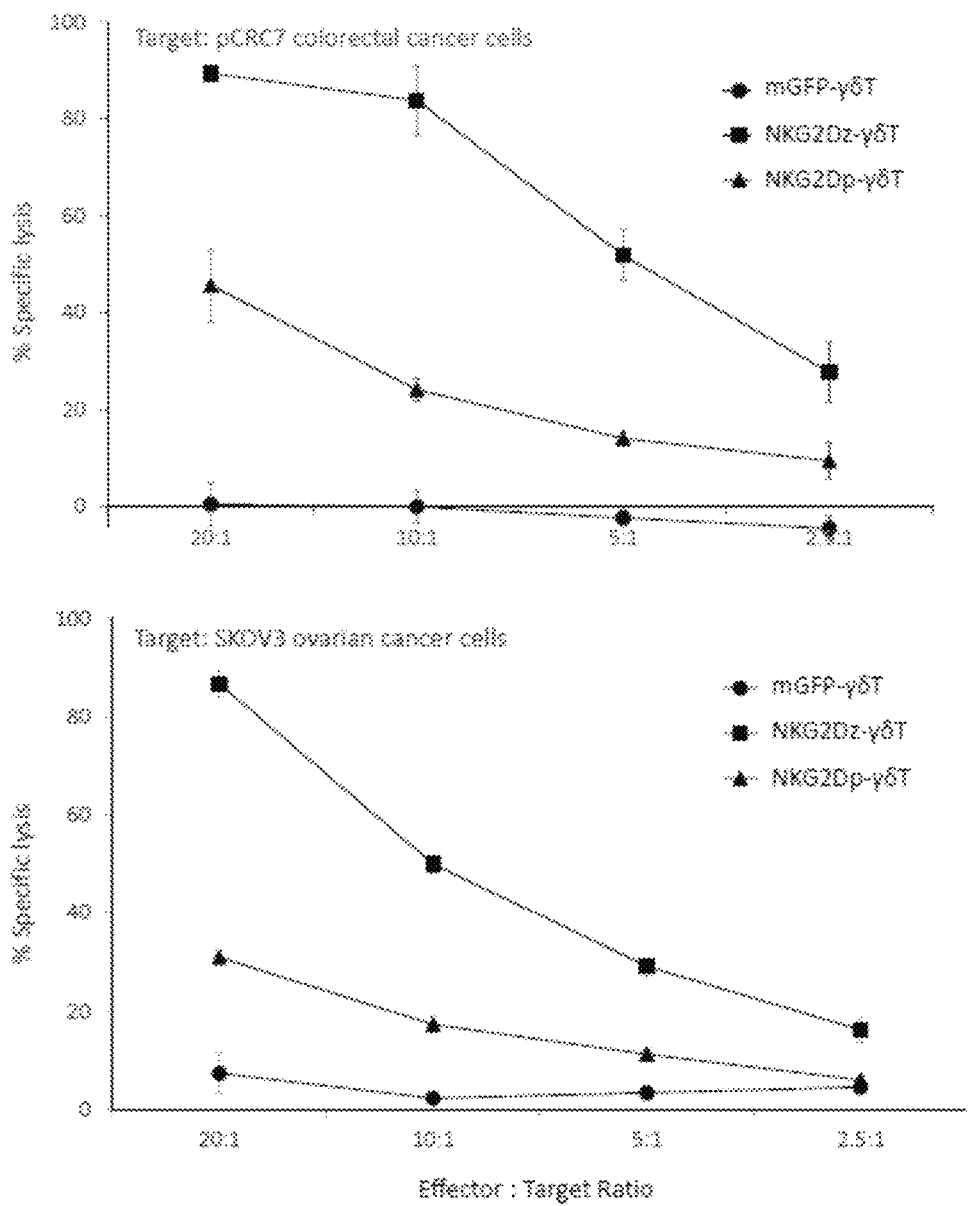
FIG. 4 shows tumor cell lysis induced by Vγ9Vδ2 T cells modified with NKG2D chimeric proteins. Delfia EuTDA cytotoxicity assay (3 hours EuTDA culturing) was used to assess tumor cell lysis efficiency. The cytotoxicity of Vγ9Vδ2 T cells against pCRC7 and SKOV3 tumor cells was observed after NKG2Dp- or NKG2Dz-mRNA electroporation, but not after mGFP electroporation. The results of one representative experiment out of three are shown.

Two NKG2D chimeric proteins containing the extracellular domain of NKG2D fused with CD3 zeta (NKG2Dz) or DAP12 (NKG2Dp) were synthesized. An mRNA electroporation approach was adopted to facilitate fast evaluation of the two constructs. mRNA electroporation was optimized in Vγ9Vδ2 T cells using EGHP mRNA, which provided almost 99% transfection efficiency. While the electroporation of Vγ9Vδ2 T cells with EGFP fused with CD3 zeta (mGFP), a control structure with EGFP to replace the extracellular domain of NKG2D, did not increase NKG2D expression, the increased NKG2D expression was observed after the electroporation of Vγ9Vδ2 T cells with NKG2Dz or NKG2Dp (FIG. 3). To determine the cytotoxicity of Vγ9Vδ2 T cells after genetic modification with the NKG2D chimeric proteins, an in vitro cytotoxicity assay was performed using the Delfia cytotoxicity kit. The same amount of mRNA for each chimeric protein was electroporated into Vγ9Vδ2 T cells. With pCRC7 human colorectal cancer cells and SKOV3 human ovarian cancer cells as the targets, the cancer cell killing efficacy of Vγ9Vδ2 T cells significantly increased 30 to 50% post NKG2Dp mRNA modification and 90% post NKG2Dz mRNA modification from less than 10% cytotoxicity observed for the mGFP control at an effector to target ratio of 20:1 (FIG. 4).

Figure 5:
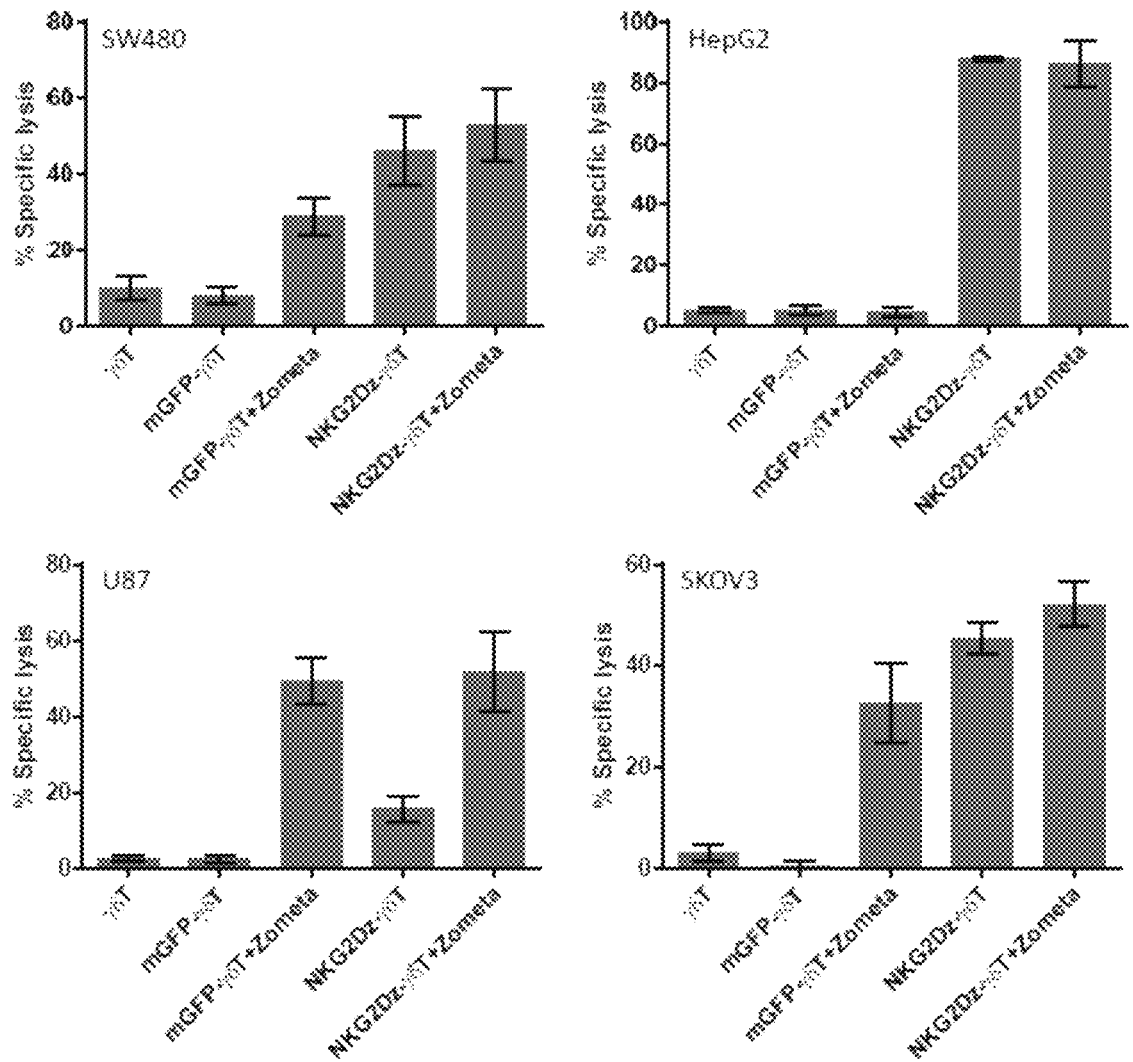
FIG. 5 shows lysis of Zometa-treated tumor cells by Vγ9Vδ2 T cells modified with NKG2Dz. Target tumor cells tested were SW480 human colon carcinoma, HepG2 human hepatocarcinoma cells, U87 human glioblastoma cells and SKOV3 human ovarian cancer cells. Tumor cells were either pre-treated with 1 μM Zometa or without Zometa treatment. Effector used are indicated. Delfia EuTDA cytotoxicity assay (3 hours EuTDA culturing) was used to assess tumor cell lysis efficiency at an effector to target ratio of 10:1. The results of one representative experiment out of three are shown.

Zometa treatment was used because Zometa can increase intracellular levels of IPP, thereby increasing the sensitivity of tumor cells to Vγ9Vδ2 T cells. Subsequently, the inventors tested whether tumor cell killing efficacy can be improved by using NKG2Dz-modified Vγ9Vδ2 T cells to kill Zometa pre-treated tumor cells at an effector to target ratio of 10:1 (FIG. 5).

It was found that without Zometa pre-treatment of tumor cells, Vγ9Vδ2 T cells or mGFP-modified Vγ9Vδ2 T cells did not kill the 4 tested tumor cell lines, namely, SW480 human colon carcinoma cells, HepG2 human hepatocarcinoma cells, U87 human glioblastoma cells and SKOV3 human ovarian cancer cells. However, NKG2Dz-modified Vγ9Vδ2 T cells were able to kill these tumor cells that were not pre-treated with Zometa, with the efficiency varying from 20 to 80%. The sensitivity of SW480, U87 and SKOV3 cells, but not HepG2 cells, towards Vγ9Vδ2 T cells were significantly increased by Zometa pre-treatment. Moreover, consistent tumor cell killing efficiencies across the 4 tested tumor cell lines were achieved when NKG2Dz-modified Vγ9Vδ2 T cells were used to kill Zometa pre-treated tumor cells. These findings indicate that while Vγ9Vδ2 T cells plus Zometa pre-treatment were able to effectively kill some types of tumor cells, the tumor-killing efficacy can be further enhanced through the modification of the effector cells with gene transfer of NKG2Dz.

Example 3—NKG2Dz-Expressing Vγ9Vδ2 T Cells Display Potent Tumor Killing Effects In Vivo To demonstrate the in vivo tumor killing effect of the NKG2Dz-modified Vγ9Vδ2 T cells, an ovarian cancer mouse model was established by inoculating via intraperitoneal (i.p.) injection of 1E7 SKOV3-Luc cells into NSG mice. 7 days post-tumor cell injection, the tumor-bearing mice were randomized into three groups (n=6) and given three different treatments intraperitoneally twice a week for 3 weeks: PBS was used as a negative control, Vγ9Vδ2 T cells (1E7 per dose) transfected with the control gene mGFP plus Zometa i.p. injection before cell injection (γδT-Z) and the NKG2Dz-modified Vγ9Vδ2 T cells (1E7 per dose) plus Zometa (NKG2D-γδ-T-Z or CAR–Vγ9Vδ2 T-cell+Zometa). Non-invasive whole-body bioluminescent imaging (BLI) of SKOV3-Luc cells were performed to monitor tumor growth.

Figure 6A:
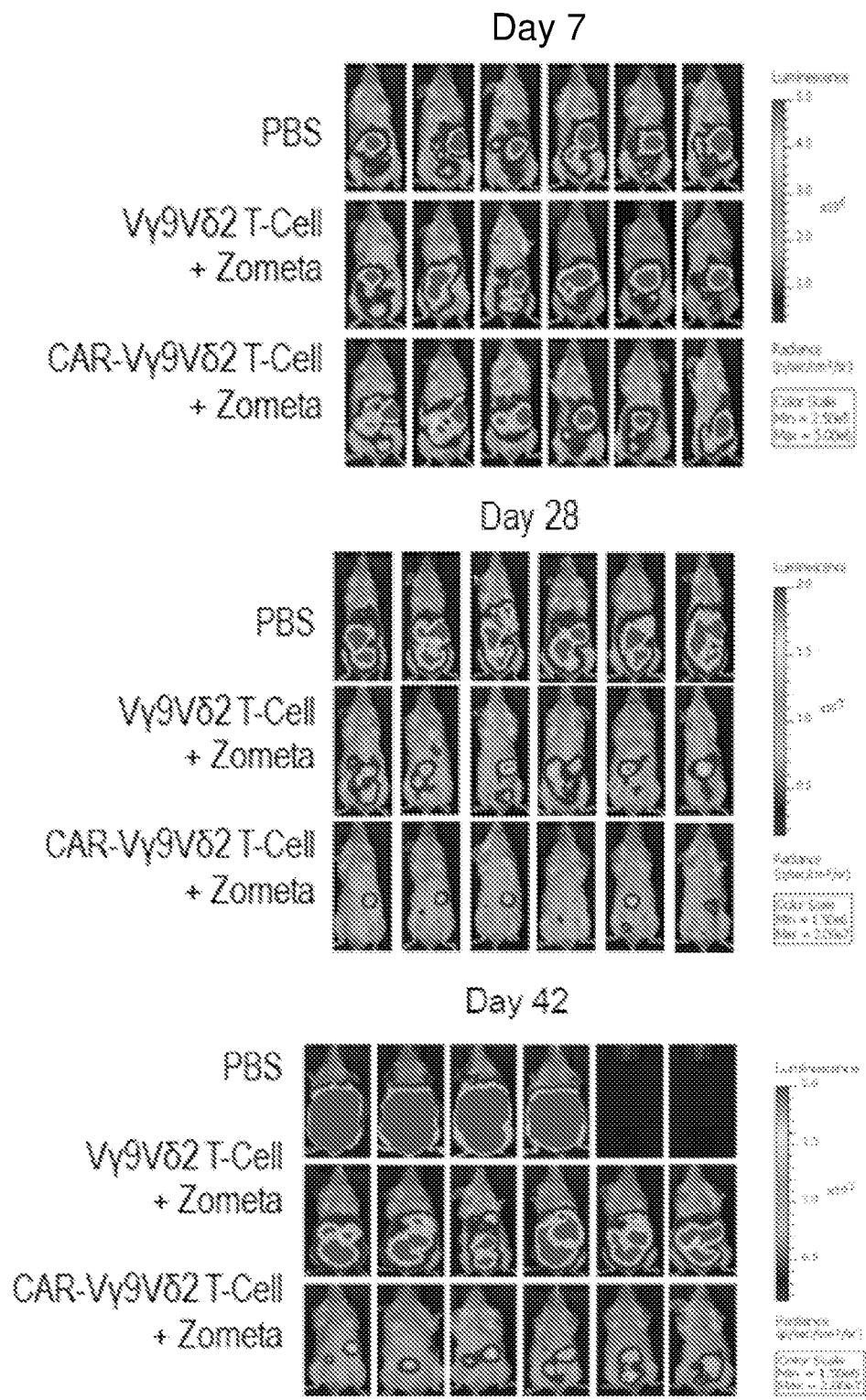
FIG. 6A to 6C show the treatment with Vγ9Vδ2 T cells electroporated with NKG2Dz mRNA results in reduction in disease burden and prolonged survival in mice with SKOV3-luc xenografts. NSG mice (n=6 per group) were i.p. injected with the SKOV3-luc human ovarian cancer cells (1E7 per mouse). The treatment started 7 days after tumor cell inoculation, twice a week for 3 weeks, 1E7 Vγ9Vδ2 T cells per injection. The mice were followed with serial weekly imaging to assess the tumor burden.
Figure 6B:
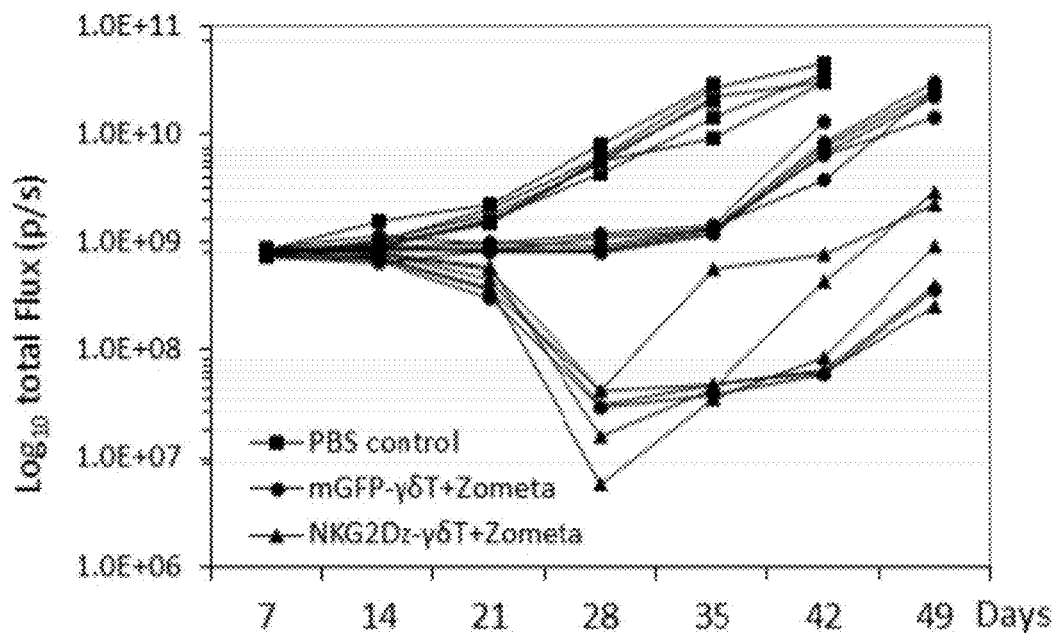
Figure 6C:
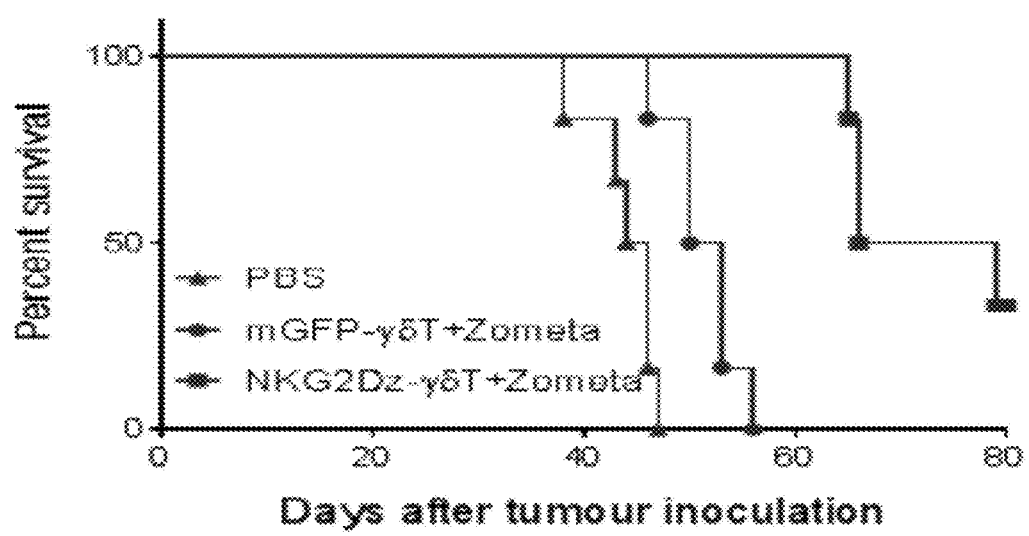

FIG. 6A shows images of mice in each group at 3 different time points post-tumor cell injection. The BLI intensities, indicative of tumor burden and distribution, demonstrated the obvious inhibitory effect of the NKG2D-γδT-Z treatment on tumor growth as compared with the PBS group and the γδT-Z group (FIG. 6B). At day 28, while established tumors continued to grow in PBS-treated mice or remained stable in mice treated with γδT-Z, the tumor burden in mice receiving the NKG2D-γδT-Z treatment was significantly reduced relative to the initial tumor burdens (P<0.001, FIG. 6B). Significant reduction of the disease by the NKG2D-γδT-Z treatment maintained for >2 weeks in 4 out of 6 treated mice. Attributed to the inhibitory effects of Vγ9Vδ2 T cells, survival of the tumor-bearing mice in the two groups receiving Vγ9Vδ2 T cell treatment was significantly prolonged (FIG. 6C). At day 48, while all mice in the PBS control group had died, 50% of the mice treated with γδT-Z and 100% of the mice treated with NKG2D-γδT-Z were still alive. The median survival times were 45 to 50 days in the two control groups, but more than 70 days in the treated group. The difference was statistically significant (p=0.0019) in logrank test). The treatment of NKG2Dz-modified Vγ9Vδ2 T cells together with Zometa resulted in significant survival advantages in tumor-bearing mice.

It should be further appreciated by the person skilled in the art that variations and combinations of features described above, not being alternatives or substitutes, may be combined to form yet further embodiments falling within the intended scope of the invention.

REFERENCES

1. Deniger D C, Maiti S N, Mi T, Switzer K C, Ramachandran V, Hurton L V, Ang S, Olivares S, Rabinovich B A, Huls M H, Lee D A, Bast R C Jr, Champlin R E, Copper L J. Activating and Propagating Polyclonal Gamma Delta T Cells with Broad Specificity for Malignancies. Clin Cancer Res. 2014 Nov. 15; 20 (22): 5708-19.
2. Dopfer E P et al. The CD3 Conformational Change in the γδ T Cell Receptor is not Triggered by Antigens but can be Enforced to Enhance Tumor Killing. Cell Rep 2014; 7: 1704-1715.
3. Du S H, Li Z, Chen C, Tan W K, Chi Z, Kwang T W, Xu X H, Wang S. Co-Expansion of Cytokine-Induced Killer Cells and Vγ9Vδ2 T Cells for CAR T-Cell Therapy. PLoS One. 2016 Sep. 6; 11 (9): e0161820.
4. Kabelitz D. Human γδ T Cells: From a Neglected Lymphocyte Population to Cellular Immunotherapy: A Personal Reflection of 30 years of γδ T Cell Research. Clin Immunol. 2016 Jul. 18. pii: S1521-6616(16)30178-4.

The invention claimed is:

1. A method of generating γδ T cells having at least one down-regulated co-inhibitory receptor, the method comprising the steps of:
   (a) culturing a population of cells comprising Vγ9Vδ2 T cells with a phosphoantigen to expand the Vγ9Vδ2 T cells;
   (b) culturing the expanded Vγ9V62T cells with artificial antigen-presenting cells expressing a Fc receptor, and an anti-CD3 antibody; and
   (c) modifying the Vγ9Vδ2 T cells to express a chimeric antigen receptor (CAR) wherein the CAR overexpresses an extracellular antigen binding domain of natural killer group 2D (NKG2D).

2. The method of claim 1, wherein the Fc receptor is CD64.

3. The method of claim 1, wherein the phosphoantigen is zoledronic acid or a salt thereof.

4. The method of claim 1, wherein the population of cells are peripheral blood mononuclear cells.

5. The method of claim 1, wherein step (a) is carried out for 7 days.

6. The method of claim 1, wherein step (b) is carried out for 10 days or more.

7. The method of claim 1, wherein the artificial antigen-presenting cells are K562 cells.

8. The method of claim 1, further comprising irradiating the artificial antigen-presenting cells prior to step (b) using gamma irradiation.

9. The method of claim 1, wherein the anti-CD3 antibody is Muromonab-CD3.

10. The method of claim 1, wherein the at least one co-inhibitory receptor is selected from the group consisting of cytotoxic T lymphocyte (CTL)-associated antigen 4 (CTLA-4/CD152); programmed cell death protein 1 (PD-1/CD279); lymphocyte activation gene-3 (LAG-3); T cell immunoglobulin and immunoreceptor tyrosine-based inhibition motif (ITIM) domain (TIGIT); T-cell immunoglobulin and mucin-containing protein 3 (TIM3); and B and T lymphocyte attenuator (BTLA).

11. The method of claim 1, wherein the modified Vγ9Vδ2 T cells have at least one up-regulated activating receptor.

12. The method of claim 1, wherein modifying the Vγ9Vδ2 T cells comprises transfecting the Vγ9Vδ2 T cells with an mRNA vector encoding the CAR.

13. The method of claim 12, wherein transfecting the Vγ9Vδ2 T cells comprises RNA electroporation.

14. The method of claim 1, wherein the CAR further comprises a signalling domain of CD3 zeta or DAP 12.

\* \* \* \* \*